(12) United States Patent
Hultgren

(10) Patent No.: US 9,622,699 B2
(45) Date of Patent: Apr. 18, 2017

(54) SYSTEM FOR MEASURING TEETH MOVEMENT AND CONTACT PRESSURE

(71) Applicant: Bruce Willard Hultgren, Victoria, MN (US)

(72) Inventor: Bruce Willard Hultgren, Victoria, MN (US)

(*) Notice: Subject to any disclaimer, the term of this patent is extended or adjusted under 35 U.S.C. 154(b) by 0 days.

(21) Appl. No.: 14/695,336

(22) Filed: Apr. 24, 2015

(65) Prior Publication Data

US 2015/0305669 A1    Oct. 29, 2015

Related U.S. Application Data

(60) Provisional application No. 61/983,879, filed on Apr. 24, 2014.

(51) Int. Cl.
| | |
|---|---|
| A61C 13/00 | (2006.01) |
| A61B 5/00 | (2006.01) |
| A61C 19/04 | (2006.01) |
| A61C 5/14 | (2006.01) |
| A61B 5/22 | (2006.01) |
| A61C 9/00 | (2006.01) |
| A61C 19/05 | (2006.01) |
| A61C 13/34 | (2006.01) |

(52) U.S. Cl.
CPC .......... *A61B 5/4547* (2013.01); *A61B 5/0022* (2013.01); *A61B 5/228* (2013.01); *A61B 5/72* (2013.01); *A61C 5/14* (2013.01); *A61C 9/0053* (2013.01); *A61C 19/04* (2013.01); *A61C 19/05* (2013.01); *A61B 5/743* (2013.01); *A61B 5/7475* (2013.01); *A61B 2560/0475* (2013.01); *A61B 2562/0219* (2013.01); *A61B 2562/0247* (2013.01); *A61B 2562/06* (2013.01); *A61C 13/0004* (2013.01); *A61C 13/34* (2013.01)

(58) Field of Classification Search
CPC ........ A61B 5/4547; A61B 5/228; A61C 19/04
See application file for complete search history.

(56) References Cited

U.S. PATENT DOCUMENTS

| | | | | |
|---|---|---|---|---|
| 3,297,021 A | * | 1/1967 | Davis ................... | A61B 5/0002 340/870.16 |
| 4,629,424 A | * | 12/1986 | Lauks .................. | A61B 5/0002 257/417 |
| 5,078,153 A | * | 1/1992 | Nordlander .......... | A61B 5/0002 128/905 |
| 5,212,476 A | * | 5/1993 | Maloney ............ | A61B 5/04886 340/4.11 |
| 5,730,151 A | * | 3/1998 | Summer ................ | A61C 19/05 600/587 |

(Continued)

*Primary Examiner* — Ralph Lewis
(74) *Attorney, Agent, or Firm* — Merchant & Gould P.C.

(57) ABSTRACT

A wearable dental apparatus for capturing dental properties of a patient includes a support structure. The support structure is configured to be worn on the dentition of the patient. The wearable dental apparatus includes at least one sensor. The sensor is coupled to the support structure. The sensor is configured to capture a series of measurement of a dental property of the patient. The measurements are associated with one or more locations on the dentition of the patient. A dental map is generated based on at least some of the measurements and is displayed. The dentition of a patient is restored by selecting a restoration material based on the measurements.

20 Claims, 17 Drawing Sheets

(56) References Cited

U.S. PATENT DOCUMENTS

| | | | | |
|---|---|---|---|---|
| 6,613,001 B1* | 9/2003 | Dworkin | ............... | A61C 7/00 |
| | | | | 600/590 |
| 7,887,324 B2* | 2/2011 | Singh | ............... | A61C 7/10 |
| | | | | 433/24 |
| 8,961,437 B2* | 2/2015 | Al-Tawil | ............... | G06F 3/011 |
| | | | | 600/590 |
| 2012/0172677 A1* | 7/2012 | Logan | ............... | A61B 5/082 |
| | | | | 600/301 |
| 2014/0152464 A1* | 6/2014 | Smith | ............... | A61F 5/566 |
| | | | | 340/870.02 |
| 2015/0305671 A1* | 10/2015 | Yoon | ............... | A61B 5/01 |
| | | | | 600/301 |

* cited by examiner

*FIG. 9*

SYSTEM FOR MEASURING TEETH MOVEMENT AND CONTACT PRESSURE

CROSS REFERENCE TO RELATED APPLICATION(S)

This application claims priority to U.S. patent application Ser. No. 61/983,879 filed on Apr. 24, 2014, entitled SYSTEM FOR MEASURING TEETH MOVEMENT AND CONTACT PRESSURE, the disclosure of which is hereby incorporated by reference in its entirety.

BACKGROUND

The masticatory force generated during biting puts pressure on the patient's dentition. Often, this force is concentrated on a few contact points between the upper and lower dentition.

A dental restoration is used to restore a tooth or multiple teeth. For example, a crown is a dental restoration that is used to restore a single tooth. A bridge is another example of a dental restoration. A bridge restores multiple teeth. In some circumstances, dental restorations are used to restore functionality after a tooth is damaged. In other circumstances, dental restorations are used to aesthetically improve a patient's dentition.

Dental restorations may be formed from many different materials. Each material has its own properties. Some materials are very strong. Other materials provide superior aesthetic properties.

SUMMARY

In general terms, this disclosure is directed to a system for measuring teeth movement and contact pressure. In one possible configuration and by non-limiting example, a dental appliance is formed to measure the pressure at various points along the dentition of the patient. In some embodiments the pressure measurements are used to design and select materials for dental restorations.

One aspect is a wearable dental appliance for capturing dental properties of a patient comprising: a support structure configured to be worn by the patient on a dentition of the patient; and at least one sensor coupled to the support structure, wherein the at least one sensor is configured to capture a series of measurements of a dental property of the patient, the measurements being associated with one or more locations on the dentition of the patient.

Another aspect is a system for capturing dental properties of a patient comprising: a wearable dental appliance comprising: a support structure configured to be worn by the patient on a dentition of the patient; and at least one sensor coupled to the support structure, wherein the at least one sensor is configured to capture a measurement of a dental property of the patient; and a computing device comprising a processing device, computer readable storage device, the computer readable storage device storing data instructions which, when executed by the processing device, cause the processing device to: receive measurements from the wearable dental appliance; associate the measurements with locations on the dentition of the patient; generate a dental map, wherein the dental map is configured to display at least some of the measurements on an image of at least a portion of the dentition of the patient.

Yet another aspect is a method of restoring the dentition of a patient comprising: capturing an impression of the dentition of the patient; fabricating a dental appliance to be worn on at least a portion of the dentition of the patient, wherein the dental appliance includes at least one sensor configured to measure a dental property of the patient; using the dental appliance to capture measurement data while the patient is wearing the dental appliance, wherein the measurement data comprises a plurality of measurements captured by the one or more sensors; associating the measurement data with one or more locations on the dentition of the patient; selecting a restoration material based in part on the measurement data; and fabricating a dental restoration for the patient, wherein the dental restoration is formed, at least in part, from the selected restoration material.

BRIEF DESCRIPTION OF THE DRAWINGS

FIG. 9 is an example measurement data table that is stored in the memory of some embodiments of the dental appliance of FIG. 1.

DETAILED DESCRIPTION

Figure 1:
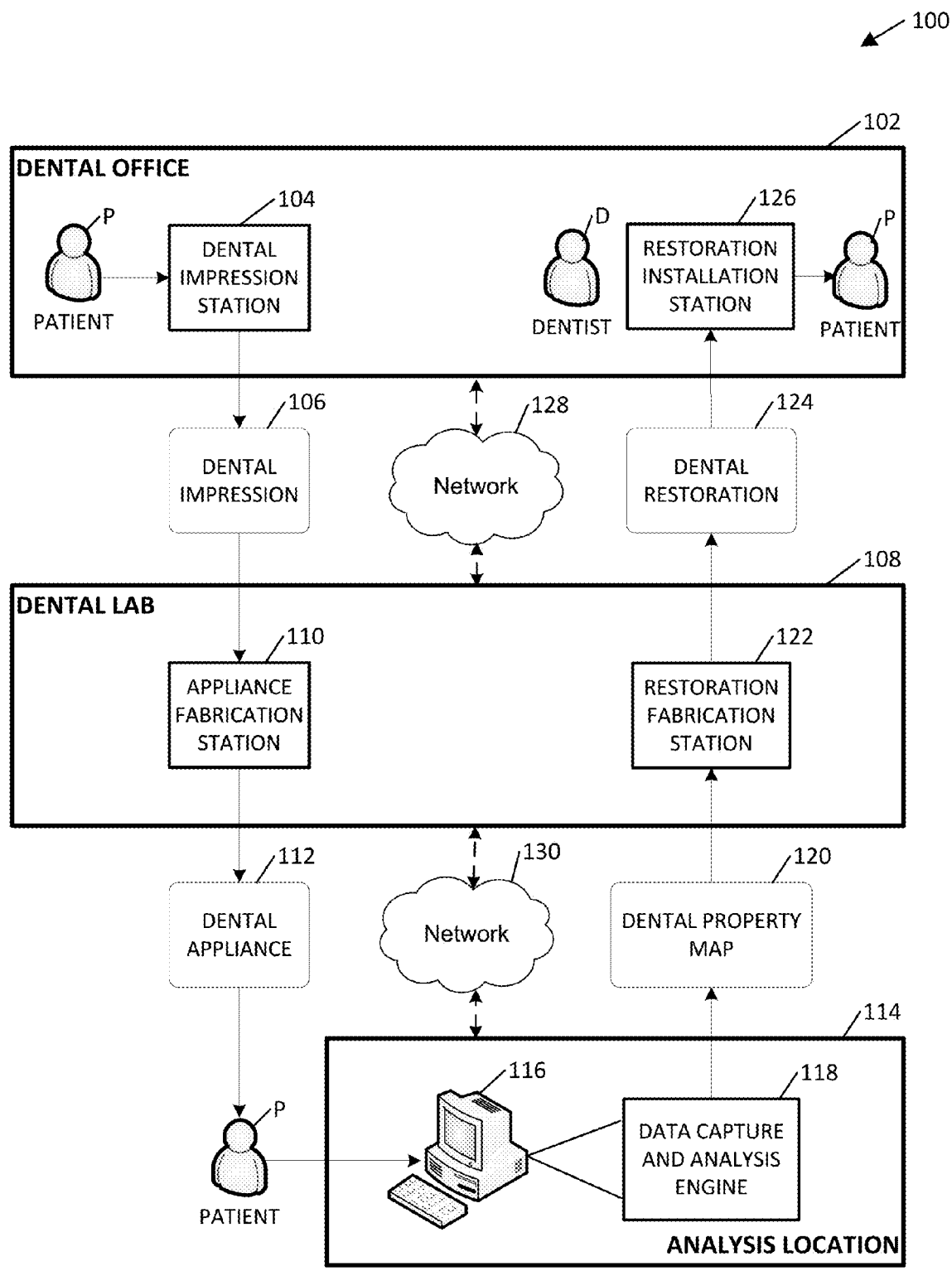
FIG. 1 is a schematic block diagram illustrating an example of a system for fabricating a dental restoration using a dental appliance for measuring teeth movement and interference.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

The present disclosure relates to a dental appliance and methods for fabricating and using the dental appliance. The dental appliance is configured to be worn over the teeth of a patient. In some embodiments, the dental appliance includes one or more measurement devices or sensors to measure properties relating to the physiology of the patient. For example, in some embodiments the dental appliance includes sensors to measure acceleration, velocity, or movement of the dentition. Additionally, in some embodiments the dental appliance includes sensors to measure force or pressure on the surface of the dentition. In some embodiments, information captured by the dental appliance is associated with a dental model of the patient's dentition. In some embodiments, the information captured by the dental appliance is used in the selection of a material for use in a dental restoration.

FIG. 1 is a schematic block diagram illustrating an example of a system 100 for fabricating a dental restoration 124 using a dental appliance 112 for measuring teeth movement and interference. In this example, the system 100 includes a dental office 102, a dental lab 108, and an analysis location 114.

The example dental office 102 includes a dental impression station 104 and a restoration installation station 126. Although shown as a single dental office in this figure, in some embodiments, the dental office 102 comprises multiple dental offices. For example, in some embodiments, the dental impression station 104 and the restoration installation station 126 are in different dental offices. Further, in some embodiments, one or both of the dental impression station 104 and the restoration installation station 126 are not in a dental office.

The example dental impression station 104 generates a dental impression 106 of the dentition of the patient P. The dental impression 106 is a geometric representation of the dentition of the patient P. In some embodiments, the dental impression 106 is a physical impression captured using an impression material, such as sodium alginate, or vinylpolysiloxane. In other embodiments, other impression materials are used as well.

In some embodiments, the dental impression 106 is a digital impression. In some embodiments, the digital impression is represented by one or more of a point cloud, a polygonal mesh, a parametric model, or voxel data. In some embodiments, the digital impression is generated directly from the dentition of the patient P, using for example an intraoral scanner. Example intraoral scanners include the TRIOS Intra Oral Digital Scanner, the Lava Chairside Oral Scanner C.O.S., the Cadent iTero, the Cerec AC, the Cyrtina IntraOral Scanner, and the Lythos Digital Impression System from Ormco. In other embodiments, a digital impression is captured using other imaging technologies, such as computed tomography (CT) or magnetic resonance imaging (MRI). In yet other embodiments, the digital impression is generated from a physical impression by scanning the impression or plaster model of the dentition of the patient P created from the physical impression. Examples of technologies for scanning a physical impression or model include three dimensional laser scanners and computed tomography (CT) scanners. In yet other embodiments, digital impressions are created using other technologies.

The example dental lab 108 includes an appliance fabrication station 110 and a restoration fabrication station 122. Although shown as a single dental lab in this figure, in some embodiments, the dental lab 108 comprises multiple dental labs. For example, in some embodiments, the appliance fabrication station 110 and the restoration fabrication station 122 are in different dental labs. Further, in some embodiments, one or both of the appliance fabrication station 110 and the restoration fabrication station 122 are not in the dental lab 108. For example, in some embodiments, one or both of the appliance fabrication station 110 and the restoration fabrication station 122 are in the dental office 102.

The example appliance fabrication station 110 fabricates a dental appliance 112 for the patient P. In some embodiments, the dental appliance is a splint or orthodontic retainer and is configured to be worn on the teeth of the patient P. In some embodiments, the dental appliance 112 is configured to measure one or more of movement, velocity, pressure, and force while the patient P is wearing the dental appliance 112. Examples of the dental appliance 112 are described in more detail in FIGS. 4-7.

The example analysis location 114 includes a computing device 116 including a data capture and analysis engine 118. In some embodiments, the patient P wears the dental appliance 112 at the analysis location 114. In other embodiments, the patient P does not visit the analysis location. Instead, the patient P wears the dental appliance 112 and then delivers it to the analysis location 114. Further, in some embodiments, the dental appliance 112 is not physically delivered to the analysis location. Instead, some or all of the data measured by the dental appliance 112 is transmitted to the analysis location 114. Although shown as a separate location in this figure, in some embodiments, the analysis location 114 is the dental office 102 or the dental lab 108. In other embodiments, the analysis location is the home of the patient.

The computing device 116 operates to generate a dental property map 120 using data representing properties measured by the dental appliance 112. In some embodiments, the dental property map 120 includes data representing properties measured by the dental appliance 112 mapped to locations on the dentition of the patient P. Further, in some embodiments, the dental property map 120 includes data corresponding to the maximum force experienced and minimum restoration material strength recommended for one or more locations on the dentition of the patient P. In some embodiments, the dental property map 120 is used to fabricate a dental restoration 124. In other embodiments, the dental property map 120 is used as a diagnostic tool to evaluate the occlusion of the patient P regardless of whether the patient needs a dental restoration. In yet other embodiments, the dental property map 120 is generated after the patient has received the new dental restoration to evaluate the occlusion of the patient after the dental restoration is installed.

The restoration fabrication station 122 operates to fabricate a dental restoration 124 for the patient P. In some embodiments, the dental restoration 124 is a filling, partial crown, full crown, veneer, or bridge. Other embodiments of the dental restoration 124 are possible as well. In some embodiments, the materials used in forming the dental restoration 124 are selected based on the dental property map 120. In some embodiments, the dental restoration 124 is formed a from an acrylic, ceramic, or metallic material. In some embodiments, the dental impression 106 is used in the fabrication of the dental restoration 124. In other embodiments, a different dental impression is used in the fabrication of the dental restoration 124. For example, in some embodiments, the dental impression 106 is captured before the dentist D has prepped the dentition of the patient P for the dental restoration 124. Accordingly, in these embodiments, another dental impression is used to fabricate the dental restoration 124.

In some embodiments, the dental restoration 124 is seated in the mouth of the patient P in the restoration installation station 126 by a dentist D. In some embodiments, the patient P may be reevaluated with a new device.

Additionally, in some embodiments, the dental office 102 is connected to the dental lab 108 by network 128. Similarly, in some embodiments, the dental lab 108 is connected by network 130 to the analysis location 114. Although not shown in this figure, in some embodiments the analysis location 114 is connected to the dental office 102 by a network as well.

The networks 128 and 130 are electronic communication networks that facilitate communication between the dental office 102, the dental lab 108, and the analysis location 114. An electronic communication network is a set of computing devices and links between the computing devices. The computing devices in the network use the links to enable communication among the computing devices in the network. The networks 128 and 130 can include routers, switches, mobile access points, bridges, hubs, intrusion detection devices, storage devices, standalone server devices, blade server devices, sensors, desktop computers, firewall devices, laptop computers, handheld computers, mobile telephones, and other types of computing devices.

In various embodiments, the networks 128 and 130 include various types of links. For example, the networks 128 and 130 can include wired and/or wireless links, including Bluetooth, ultra-wideband (UWB), 802.11, ZigBee, and other types of wireless links. Furthermore, in various embodiments, the networks 128 and 130 are implemented at various scales. For example, the networks 128 and 130 can be implemented as one or more local area networks (LANs), metropolitan area networks, subnets, wide area networks (such as the Internet), or can be implemented at another scale. Further, in some embodiments, the network 128 and network 130 are the same network, such as the Internet or another network.

Figure 2:
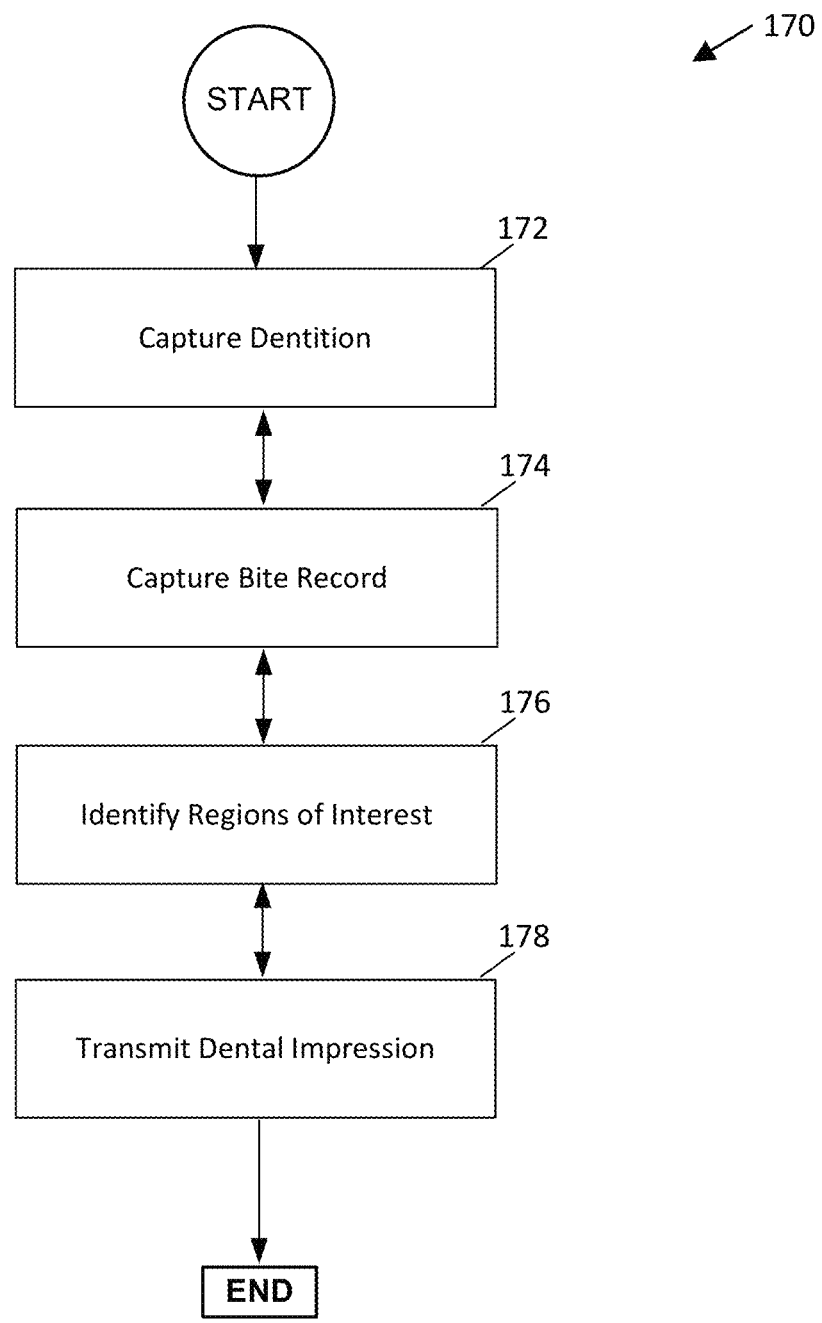
FIG. 2 is an example process performed in some embodiments of the dental impression station of FIG. 1.

FIG. 2 is an example process 170 performed at some embodiments of the dental impression station 104.

First, at operation 172, the dentition of the patient P is captured. As described above with respect to FIG. 1, in some embodiments, the dentition is captured using a physical impression material and in other embodiments, the dentition is captured using a digital impression system.

Next, at operation 174, the bite record of the patient P is captured. In some embodiments, the bite record comprises information about contact between the upper dentition and lower dentition of the patient. In some embodiments, the bite record is captured in one or more of following positions: centric occlusion, centric relation, and various excursive bite positions. In some embodiments, this operation is not performed and the bite record is not captured.

In some embodiments, the bite record is captured using a bite registration material such as bite registration wax or polysiloxane. A bite registration material captures the relationship between the upper and lower dentition of the patient P as indents when the patient P bites into the material. In some embodiments, the contact regions are identified as holes or thin regions in the bite registration material.

In other embodiments, the bite record of the patient P is captured using a marking paper, such as articulating or occlusal marking paper or film. In these embodiments, the patient P bites down on the marking paper. Material from the marking paper transfers to the teeth of the patient P in the contact regions. These marks on the teeth of the patient can then be recorded in a photograph or manually on a tooth chart.

Next, at operation 176, one or more regions of interest are identified. In some embodiments, a group of teeth, a tooth, or a particular region of a tooth is identified as an area of interest. Example areas of interest include the lower, right quadrant; the lower, right second molar; and the distal-lingual cusp of the lower, right second molar. In some embodiments, the regions of interest are identified based on planned locations for dental restorations. For example, if the dentist D is planning to replace the upper, left cuspid with a crown, that tooth may be identified as a region of interest. Additionally, in some embodiments, regions of interest are identified based on the contact points in the bite record captured during operation 174. Further, in some embodiments, regions of interest are identified based on wear patterns on the dentition of the patient P. However, in some embodiments, this operation is not performed.

Next, at operation 178, the dental impression 106 is transmitted. In some embodiments, the dental impression 106 is transmitted to the dental lab 108. In some embodiments, the bite record captured in operation 174 and the regions of interest identified in operation 176 are transmitted with the dental impression 106. In some embodiments, the dental impression 106 is transmitted across the network 128 as a digital impression. In other embodiments, the dental impression 106 is transmitted as a physical dental impression or dental model.

Figure 3:
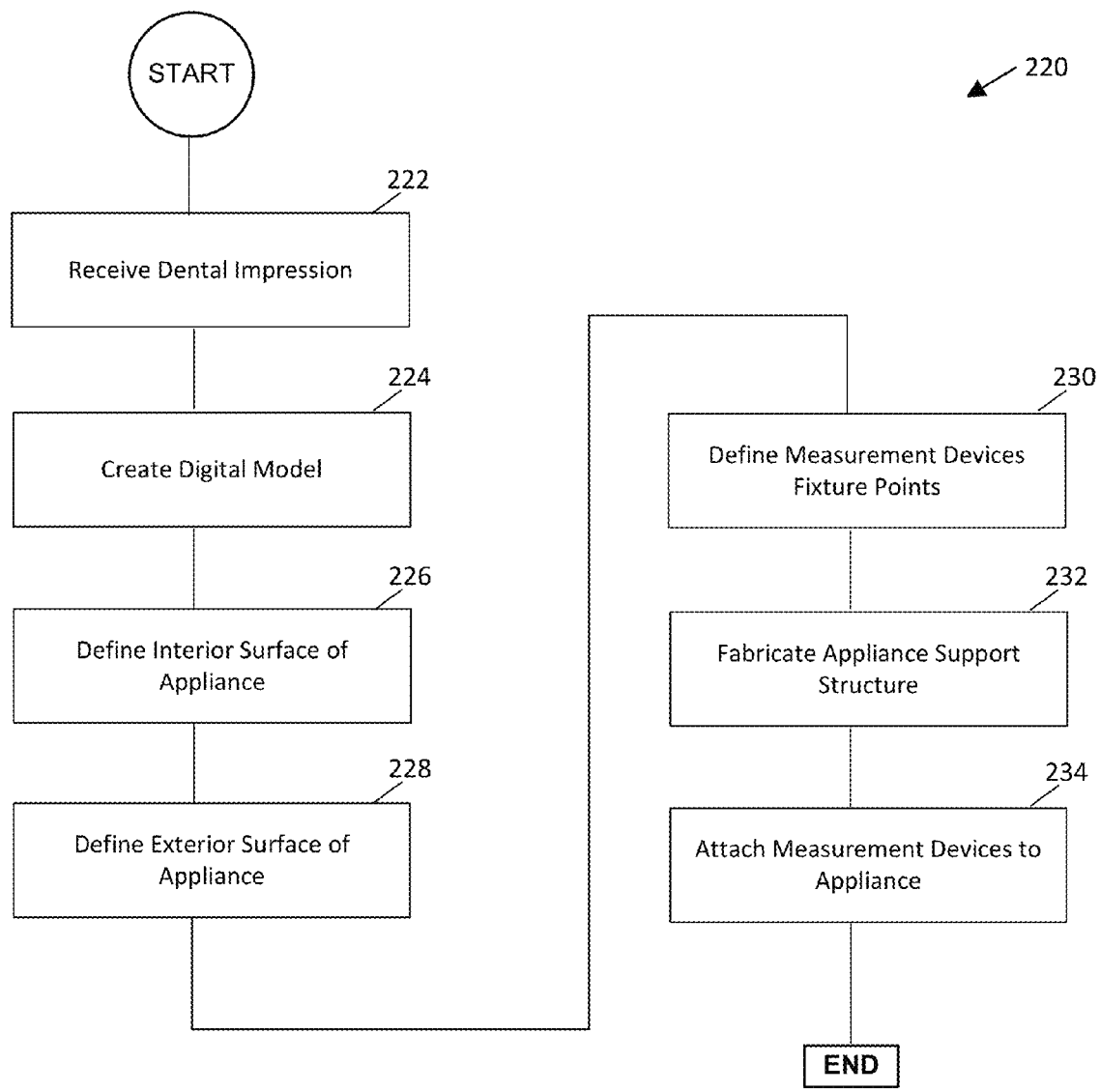
FIG. 3 is an example process of fabricating the dental appliance of FIG. 1.

FIG. 3 is an example process 220 of fabricating the dental appliance 112. In some embodiments, process 220 is performed at the appliance fabrication station 110.

First, at operation 222, the dental impression 106 is received. As described above with respect to FIGS. 1-2, in some embodiments, the dental impression 106 is a physical dental impression, a physical dental model, or a digital impression. Additionally, in some embodiments, the dental impression 106 includes bite record information or information about regions of interest.

Next, at operation 224, a digital model is created. The digital model is created from the dental impression 106. The digital model is a three-dimensional model representing the surface of the dentition of the patient P. In some embodiments, the digital model is formed by scanning a plaster model with a three-dimensional laser scanner.

Next, at operation 226, the interior surface of the appliance is defined. The interior surface of the dental appliance 112 is formed to closely follow the exterior surface of the digital model of the dentition of the patient P. For example, in some embodiments, the inner surface of the dental appliance 112 is formed by offsetting or expanding the exterior surface of the digital model by a predetermined factor.

Next, at operation 228, the exterior surface of the dental appliance 112 is defined. In some embodiments, the exterior surface of the dental appliance 112 is formed by offsetting or expanding the interior of the dental appliance 112 by the thickness of the dental appliance 112. In some embodiments, the thickness of the dental appliance 112 is between 1 mm and 6 mm. In other embodiments, the dental appliance 112 is thicker or thinner. Further, in some embodiments, the thickness of the dental appliance 112 is uniform, while in other embodiments, the thickness of the dental appliance 112 is nonuniform.

Next, at operation 230, one or more sensor fixture points are defined. The sensor fixture points are configured to secure sensors to the dental appliance 112. In some embodiments, the sensor fixture points are slots. Other embodiments of the sensor fixture points are possible as well. Additionally, some embodiments include tracks in the exterior surface of the dental appliance 112 to allow wires to run to the sensor fixture points. Sensor fixture points are illustrated and described in greater detail with respect to FIG. 7.

Next, at operation 232, the support structure of the dental appliance 112 is fabricated. In some embodiments, the support structure of the dental appliance 112 is fabricated using a rapid fabrication machine. One example of a rapid fabrication machine is a three-dimensional printer, such as the ProJet line of printers from 3D Systems, Inc. of Rock Hill, S.C. Another example of a rapid fabrication machine is a milling device, such as a computer numerically controlled (CNC) milling device.

In alternative embodiments, the support structure is fabricated using other fabrication technologies such as by using a dental vacuum form machine with a physical dental model.

Next, at operation 234, the sensors are attached to the support structure of the dental appliance 112. In some embodiments, the sensors are secured in the slots with an adhesive. In other embodiments, the sensors are mechanically secured instead.

Figure 4:
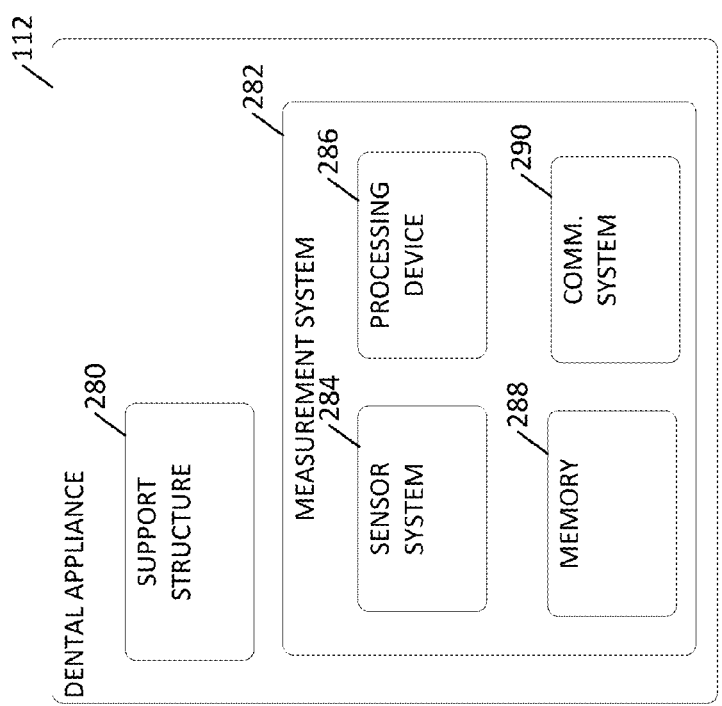
FIG. 4 is a schematic block diagram of an embodiment of the dental appliance of FIG. 1.

FIG. 4 is a schematic block diagram of an embodiment of the dental appliance 112. The dental appliance 112 includes a support structure 280 and a measurement system 282.

The support structure 280 is a physical structure that is configured to couple to the dentition of the patient P. In some embodiments, the support structure 280 is configured to fit over some or all of the lower teeth of the patient P. In other embodiments, the support structure 280 is configured to fit over some or all of the upper teeth of the patient P. Examples of the support structure 280 include dental splints and orthodontic retainers. In some embodiments, the support structure 280 is formed from a rigid or semi-rigid material, such as plastic or a composite material.

In some embodiments, the support structure 280 is formed from multiple rigid or semi-rigid components that are flexibly connected, such that each of the rigid or semi-rigid components moves independently of the rest of the support structure 280. In this manner, the dental appliance 112 is configured to measure the movement of various teeth or groups of teeth independently. In another embodiment, the support structure 280 is formed from a thin, flexible film. In this manner, the effect of the support structure 280 on the movement of teeth is minimized. This allows for more accurate measurement of the properties of the dentition of the patient P.

The measurement system 282 is a system configured to measure a property of the dentition of the patient, such as acceleration, velocity, or movement of the dentition or portions of the dentition and pressure due to masticatory force at points along the dentition. In some embodiments, the measurement system measures one or both of clenching pressure and bruxing pressure, which may include static compressive stresses and shear stresses. In some embodiments, the measurement system 282 includes a sensor system 284, a processing device 286, a memory 288, and a communication system 290.

The sensor system 284 comprises one or more sensors configured to measure a property of the dentition of the patient P. In some embodiments, the sensors are disposed at various locations relative to the dentition of the patient P. In these embodiments, the sensors measure properties of the dentition of the patient P at these various locations. An example embodiment of the dental appliance 112 with multiple sensors disposed at various locations is shown and described with respect to FIG. 5.

In some embodiments, the sensor system 284 includes one or more piezoelectric pressure sensors. A piezoelectric pressure sensor is formed from a piezoelectric material such as various crystals or ceramics. In some embodiments, the piezoelectric pressure sensor is formed from a thin film of piezoelectric material such as metallized piezo film from Measurement Specialties in Hampton, Va. In response to mechanical pressure or stress, a piezoelectric material accumulates electric charge. By measuring the accumulated electrical charge, the mechanical pressure or stress can be inferred. In some embodiments of the sensor system 284, piezoelectric sensors are disposed in the support structure 280 so as to be adjacent to the occlusal surface of the dentition of the patient P when the dental appliance 112 is worn. In this manner, the sensor system 284 measures the pressure at various points on the dentition of the patient P.

Further, in some embodiments, the sensor system 284 includes one or more accelerometers. An accelerometer is a device that is used to measure acceleration, including gravitational acceleration. In some embodiments, an accelerometer measures acceleration in three dimensions. In these embodiments, the orientation of the accelerometer is inferred by comparing the measured direction and magnitude of the acceleration to the expected direction and magnitude of gravitational acceleration. Additionally, in some embodiments, the motion of the accelerometer is inferred. In some embodiments of the dental appliance 112, one or more accelerometers are used to infer the orientation of the dental appliance 112 and the movement of the dental appliance 112. In this manner, the orientation and movement of the dentition of the patient P may be inferred as well. In some embodiments, multiple accelerometers are included to determine relative movement of portions of the dentition. In alternate embodiments, one or more accelerometers are coupled to the support structure 280 and one or more accelerometers are coupled to the opposing dentition of the patient. In this manner, the movement of the mandible of the patient is inferred based on the difference in the movements detected between the accelerometers coupled to the upper and lower dentition of the patient P.

In some embodiments, the sensor system 284 includes a combination of piezoelectric sensors and accelerometers. Additionally, in some embodiments of the sensor system 284 other types of sensors are included as well.

The processing device 286 is a device that is configured to capture signals from the sensor system 284. In some embodiments, the processing device 286 is a digital signal processor. In other embodiments, the processing device 286 is central processing unit (CPU). Yet other embodiments of the processing device 286 are possible as well. In some embodiments, the processing device 286 captures signals from the sensor system 284 on a regular interval, such as once per millisecond. Other embodiments use shorter or longer intervals. In some embodiments, the processing device 286 captures signals from the sensor system 284 when one or more of the sensors generate a signal that is greater than a predetermined threshold.

In some embodiments, the processing device 286 records the signals from the sensor system 284 in the memory 288. In some embodiments, the processing device 286 records additional information in the memory as well, such as the date and time the signal was captured and an identifier of the sensor from which the signal was captured. In some embodiments, the date and time information is used to evaluate physiological parameters for extended periods of time, such as all night while the patient P is sleeping. In some embodiments, other additional information is recorded as well. An example data table of sensor measurements is shown and described in more detail with respect to FIG. 9.

In addition, in some embodiments, the processing device 286 transmits and receives instructions or data using the communication system 290.

The memory 288 is a device for storing digital data and includes computer readable media. Examples of computer readable media include, but are not limited to, random access memory, read only memory, electrically erasable programmable read only memory, flash memory, or other memory technology.

The communication system 290 is a device for transmitting and receiving signals corresponding to data or instructions. In some embodiments, the communication system 290 is configured to transmit and receive signals via a wire or cable, such as a mini USB cable, a micro USB cable, or an IEEE 1394 cable, as well as other parallel or serial cables. In other embodiments, the communication system 290 is configured to transmit and receive signals wireless using a wireless protocol, such as Bluetooth, ultra-wideband (UWB), 802.11, ZigBee, and other types of wireless protocols.

Some embodiments of the measurement system 282 do not include one or all of the processing device 286, the memory 288, and the communication system 290. Advantageously, these embodiments may be less expensive to manufacturer.

Figure 5:
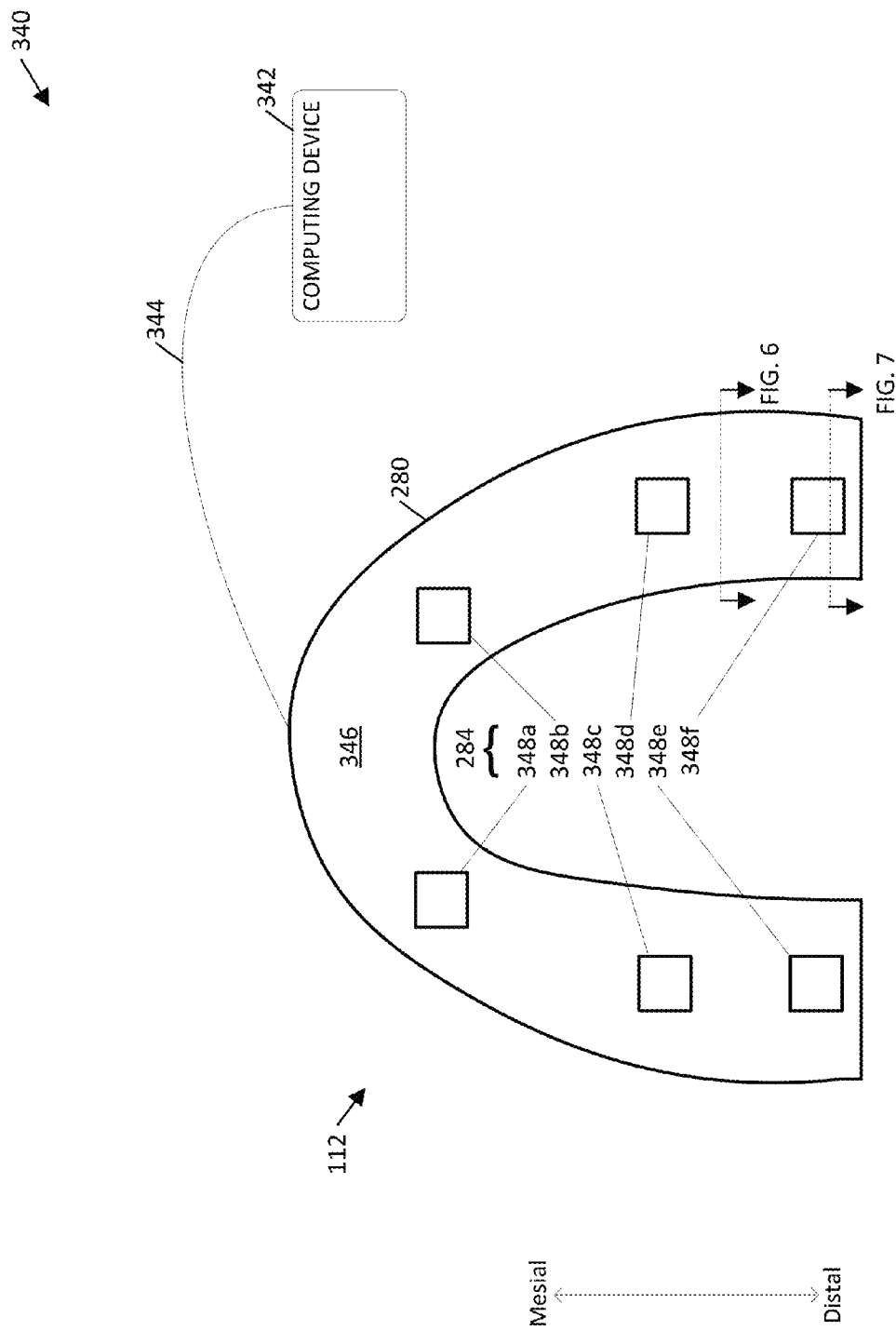
FIG. 5 is a schematic illustration of an example dental appliance analysis system including the dental appliance and computing device of FIG. 1.

FIG. 5 is a schematic illustration of an example dental appliance analysis system 340. The dental appliance analysis system 340 includes the dental appliance 112 and the computing device 116. In the example shown, the dental appliance 112 and the computing device 116 are connected via cable 344. Also shown is the exterior surface 346 of the dental appliance 112 and the sensor system 284 including sensors 348a-f.

In the example shown, the dental appliance 112 is configured to be worn on the upper dentition of the patient P. The interior surface (not shown) of the dental appliance 112 is configured to fit over the exterior surface of the upper dentition of the patient P. The exterior surface 348 is configured to contact the opposing dentition of the patient P. The exterior surface 348 is shown and described in more detail with respect to FIGS. 6-7.

In the example shown, the sensors 348a-f are devices for measuring a property. As described with respect to FIG. 4, examples of sensors 348a-f include, but are not limited to, piezoelectric pressure sensors and accelerometers.

The sensors 348a-f are disposed along the exterior surface 346 of the dental appliance 112. Thus, the sensors 348a-f are disposed to contact the opposing dentition. In this manner, pressure is applied to the sensors 348a-f through contact with the opposing dentition. In some embodiments, sensors are disposed in other locations as well, such as along the buccal or lingual surface of the dentition.

In the embodiment shown, the sensors 348a-f are disposed around the dentition of the patient. Sensor 348a is disposed at a position on the dental appliance 112 that is near the left, upper cuspid of the patient P when the dental appliance 112 is being worn. Similarly, sensor 348b is near the right, upper cuspid; sensor 348c, the left first molar; sensor 348d, the right first molar; sensor 348e, the left second molar; and sensor 348f, the right second molar. Although the embodiment shown includes six sensors 348a-f, other embodiments are possible with more or fewer sensors. For example, in some embodiments, one or more sensors are included for each tooth in the dentition. Additionally, in some embodiments, the sensors are not arranged symmetrically. Further, in some embodiments, only a single sensor is included. In some embodiments, the locations of the sensors are defined based on the regions of interest to the dentist D.

The computing device 116 operates to receive signals from the dental appliance 112. In some embodiments, the computing device 116 sends instructions or configuration information to the measurement system 282. In some embodiments, the computing device 116 is in electrical communication with the measurement system 282, such as by cable 344. Embodiments of the computing device 116 are illustrated and described in more detail with respect to FIG. 8.

In other embodiments, the computing device 116 and the measurement system 282 communicate wirelessly, using a wireless protocol, such as Bluetooth, ultra-wideband (UWB), 802.11, ZigBee, and other types of wireless protocols. In some of these embodiments, the dental appliance 112 periodically checks whether the computing device 116 is available for wireless communication (e.g., when the dental appliance is in the proximity of the computing device 116).

In some embodiments, the dental appliance 112 transmits signals representing measurements to the computing device 116 when it is able to communicate with the computing device 116. In some embodiments, the dental appliance 112 deletes the measurements from the memory 288 after confirming the measurements were transferred to the computing device 116.

In alternate embodiments, the dental appliance 112 does not include the memory 288. In these embodiments, the signals representing the measurements are transmitted to the computing device 116 as the properties are measured by the sensor system 284. In these embodiments, measurements are only collected from the dental appliance 112 while it is connected to the computing device 116.

Further, although FIG. 5 describes communication occurring between the dental appliance 112 and the computing device 116 at the analysis location 114, in some embodiments, the dental appliance 112 communicates with a different computing device. For example, in some embodiments, the dental appliance 112 communicates with a personal computer or smart phone of the patient P. In these embodiments, the computing device does not include the data capture and analysis engine 118. Instead, the computing device transmits the data that is captured to the computing device 116 at the analysis location 114.

Figure 6:
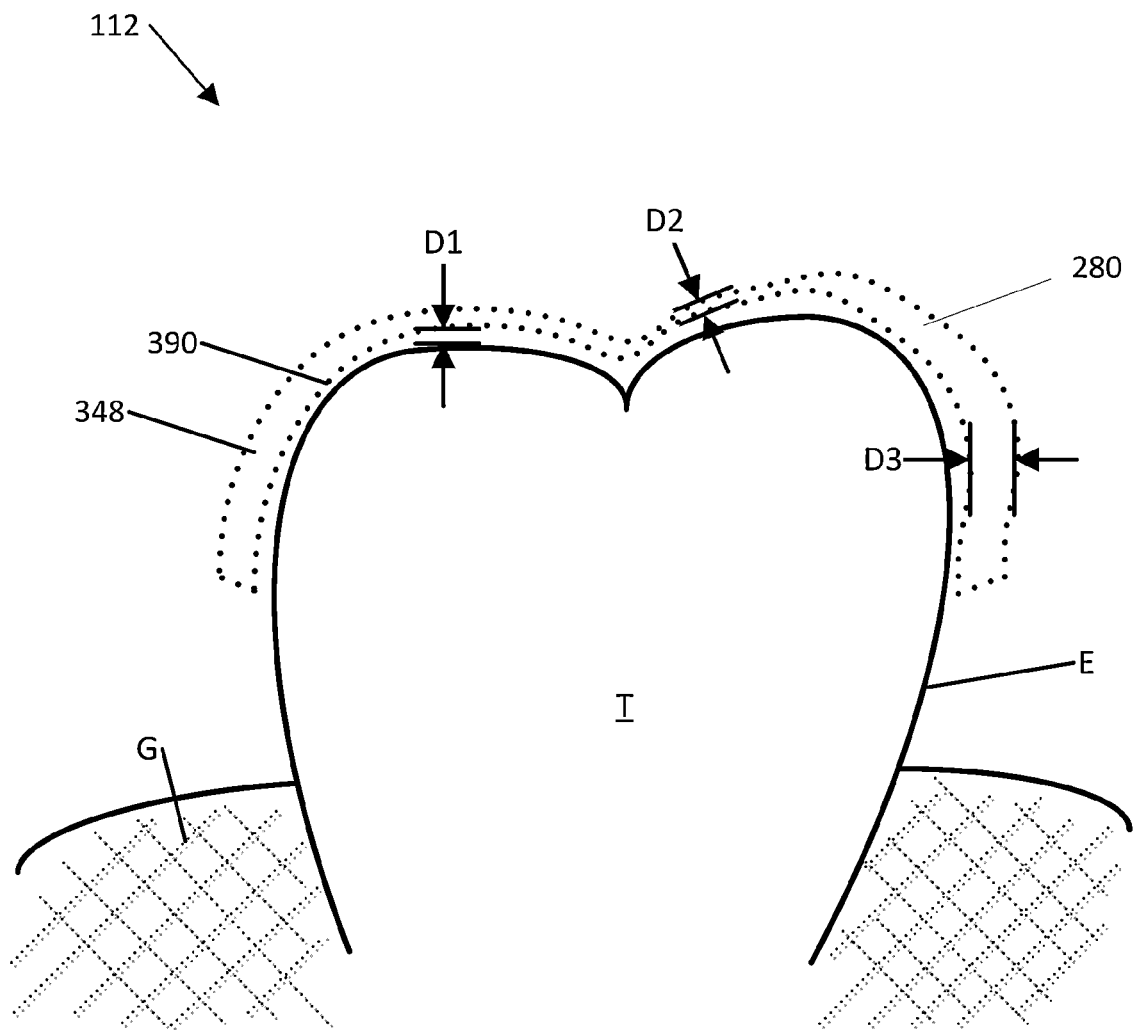
FIG. 6 is a cross-sectional view of an embodiment of the dental appliance of FIG. 1 on the dentition of the patient.

FIG. 6 is a cross-sectional view of an embodiment of the dental appliance 112 being worn over the dentition of a patient P. The dental appliance 112 includes the support structure 280 including an exterior surface 348 and an interior surface 390. The dentition includes a tooth T and gingiva G. The tooth includes an exterior surface E.

The interior surface 390 is configured to follow the contour of the exterior surface E of the tooth T. In some embodiments, the interior surface 390 is offset from the exterior surface E of the tooth T by a distance D1. The offset may make it easier to position and remove the dental appliance 112 from the dentition of the patient P.

Similarly, the exterior surface 348 is generally configured to match the contour of the interior surface. In some embodiments, the thickness of the support structure 280 is uniform. In other embodiments, the thickness of the support structure 280 is nonuniform. For example, in the embodiment shown, the portions of the support structure 280 that interfere with the bite (e.g., potential contact points) have a thickness of D2, while regions that are not likely to interfere have a thickness of D3. In some embodiments, the thickness D2 is smaller than the thickness D3. In this manner, the support structure 280 is configured to minimize interference with bite of the patient P, and the measurements captured by the dental appliance 112 are more reflective of the actual bite of the patient P.

Figure 7:
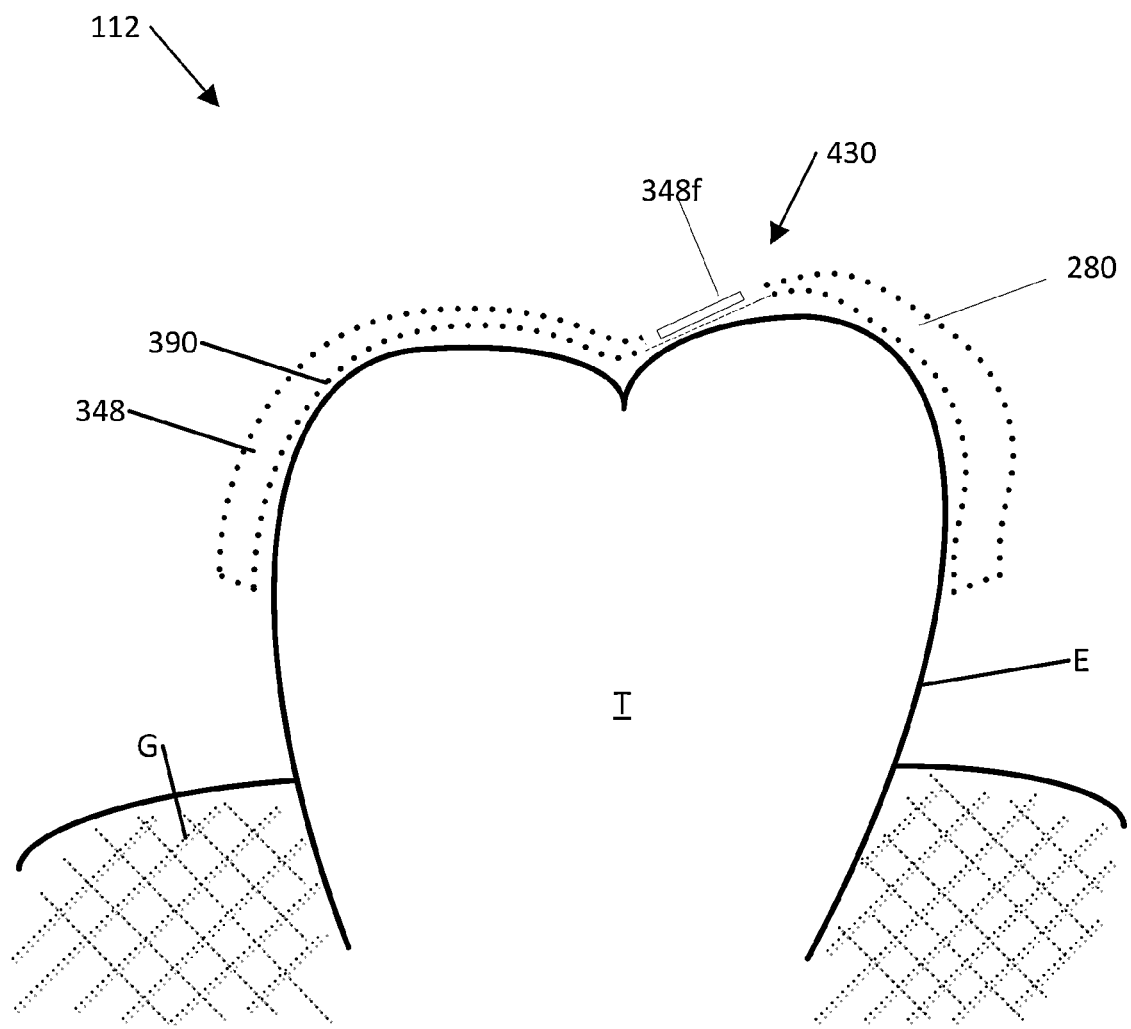
FIG. 7 is a cross-sectional view of an embodiment of the dental appliance of FIG. 1, including a sensor, on the dentition of the patient.

FIG. 7 is a cross-sectional view of an embodiment of the dental appliance 112, including the sensor 348*f*, being worn over the dentition of a patient P. The dental appliance 112 includes the support structure 280 including an exterior surface 348, an interior surface 390, and a sensor fixture point 430. The dentition includes a tooth T and gingiva G. The tooth includes an exterior surface E.

The sensor fixture point 430 is a portion of the support structure 280 that is configured to secure the sensor 348*f*. In some embodiments, the sensor fixture point 430 is a hole in the surface of the support structure 280. In other embodiments, the sensor fixture point 430 is a thinner area of the support structure 280 that serves as a bed for the sensor 348*f*. In some embodiments, the sensor 348*f* is secured to the support structure 280 with an adhesive. In alternate embodiments, the support structure 280 includes mechanical mechanisms to secure the sensor 348*f*, such as a slot that the sensor 348*f* is slid into, arms that cross over the sensor 348*f*, or pegs that the sensor 348*f* slides onto. Other embodiments of sensor fixture point 430 are possible as well.

Figure 8:
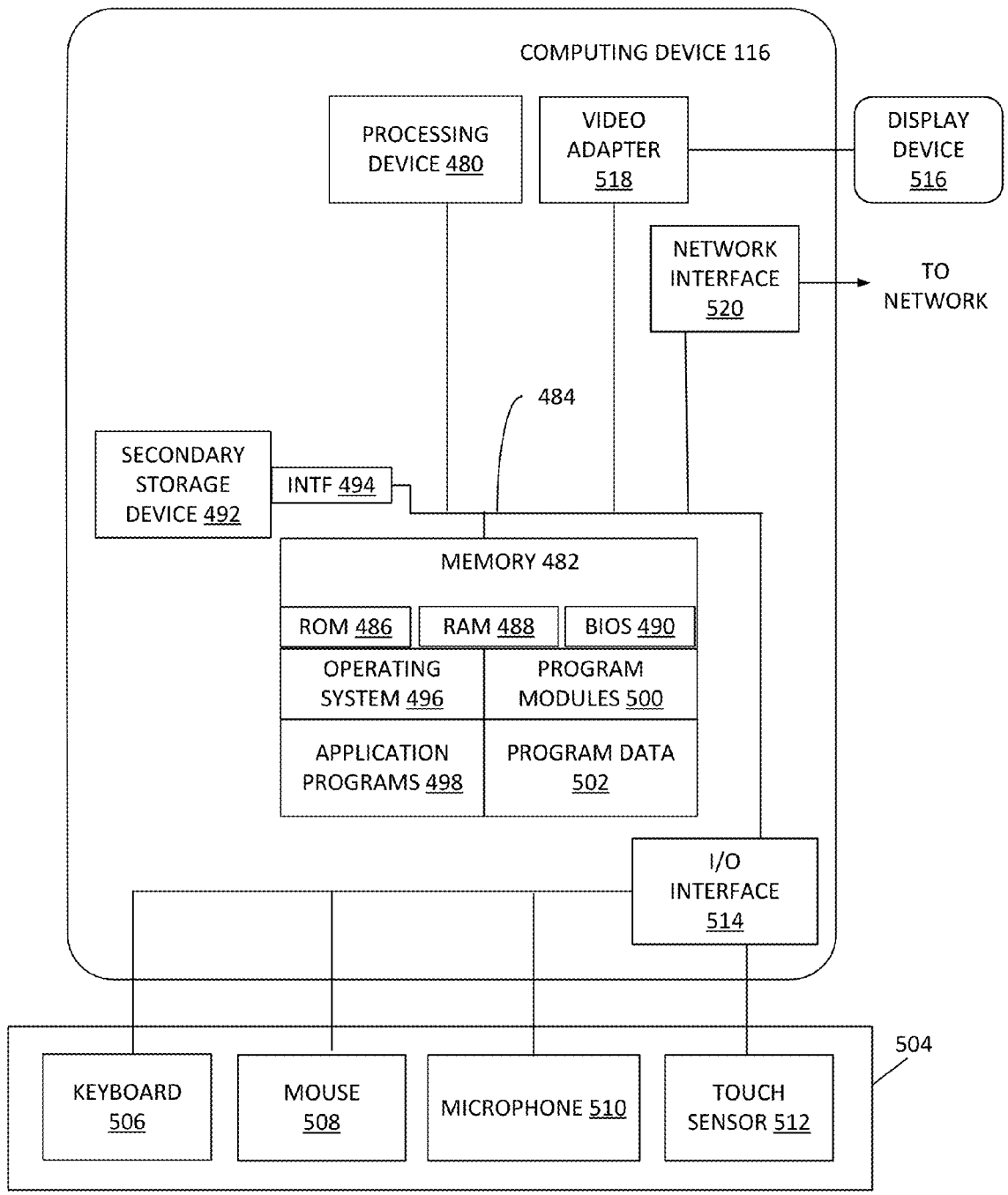
FIG. 8 illustrates an example architecture of a computing device, which can be used to implement aspects according to the present disclosure.

FIG. 8 illustrates an exemplary architecture of a computing device that can be used to implement aspects of the present disclosure, including any of the plurality of computing devices described herein, such as a computing device of the dental impression station 104, the analysis location 114, the appliance fabrication station 110, the restoration fabrication station 122, or any other computing devices that may be utilized in the various possible embodiments.

The computing device illustrated in FIG. 8 can be used to execute the operating system, application programs, and software modules (including the software engines) described herein. By way of example, the computing device will be described below as the computing device 116 that operates the data capture and analysis engine 118. To avoid undue repetition, this description of the computing device will not be separately repeated herein for each of the other possible computing devices, but such devices can also be configured as illustrated and described with reference to FIG. 8.

The computing device 116 includes, in some embodiments, at least one processing device 480, such as a central processing unit (CPU). A variety of processing devices are available from a variety of manufacturers, for example, Intel or Advanced Micro Devices. In this example, the computing device 116 also includes a system memory 482, and a system bus 484 that couples various system components including the system memory 482 to the processing device 480. The system bus 484 is one of any number of types of bus structures including a memory bus, or memory controller; a peripheral bus; and a local bus using any of a variety of bus architectures.

Examples of computing devices suitable for the computing device 116 include a desktop computer, a laptop computer, a tablet computer, a mobile computing device (such as a smart phone, an iPod® or iPad® mobile digital device, or other mobile devices), or other devices configured to process digital instructions.

The system memory 482 includes read only memory 486 and random access memory 488. A basic input/output system 490 containing the basic routines that act to transfer information within computing device 116, such as during start up, is typically stored in the read only memory 486.

The computing device 116 also includes a secondary storage device 492 in some embodiments, such as a hard disk drive, for storing digital data. The secondary storage device 492 is connected to the system bus 484 by a secondary storage interface 494. The secondary storage devices 492 and their associated computer readable media provide non-volatile storage of computer readable instructions (including application programs and program modules), data structures, and other data for the computing device 116.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 492 or system memory 482, including an operating system 496, one or more application programs 498, other program modules 500 (such as the software engines described herein), and program data 502. The computing device 116 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 116 through one or more input devices 504. Examples of input devices 504 include a keyboard 506, mouse 508, microphone 510, and touch sensor 512 (such as a touchpad or touch sensitive display). Other embodiments include other input devices 504. The input devices are often connected to the processing device 480 through an input/output interface 514 that is coupled to the system bus 484. These input devices 504 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 516, such as a monitor, liquid crystal display device, projector, or touch sensitive display device, is also connected to the system bus 484 via an interface, such as a video adapter 518. In addition to the display device 516, the computing device 116 can include various other peripheral devices (not shown), such as speakers or a printer.

When used in a local area networking environment or a wide area networking environment (such as the Internet), the computing device 116 is typically connected to the network through a network interface 520, such as an Ethernet interface. Other possible embodiments use other communication devices. For example, some embodiments of the computing device 116 include a modem for communicating across the network.

The computing device 116 typically includes at least some form of computer readable media. Computer readable media includes any available media that can be accessed by the computing device 116. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 116.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 8 is also an example of programmable electronics, which may include one or more such computing devices, and when multiple computing devices are included, such computing devices can be coupled together with a suitable data communication network so as to collectively perform the various functions, methods, or operations disclosed herein.

Figure 9:
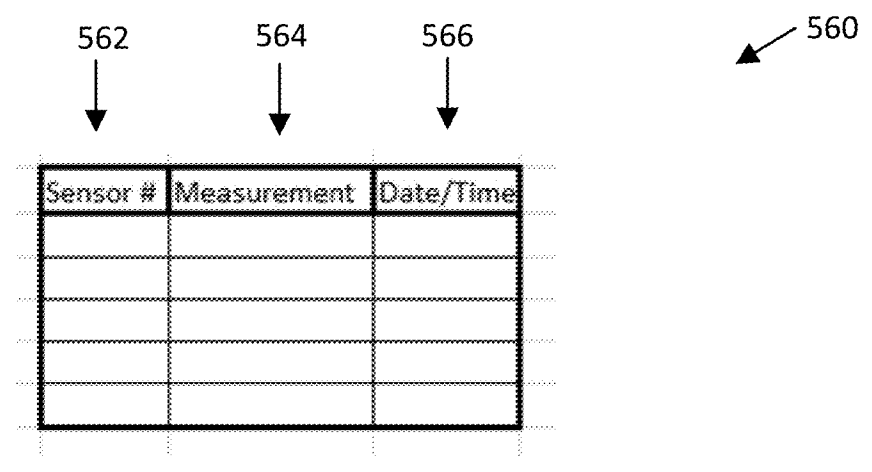

FIG. 9 is an example measurement data table 560 that is stored in the memory 288 of some embodiments of the dental appliance 112. The measurement data table 560 stores measurements captured by the dental appliance 112. In some embodiments, the measurement data table 560 is stored in the computing device 116 instead of or in addition to being stored in the memory 288.

In the measurement data table 560, the first column 562 stores a sensor identification value, such as a sensor number. The second column 564 stores a measurement value representing the property measured by the sensor. The third column 566 stores a date and time value representing the date and time the measurement was captured. In operation, the measurement data table 560 is populated with a plurality of records representing measurements captured by the sensors 348a-f of the dental appliance 112. In some embodiments, the measurement data table 560 includes additional, fewer, or different columns.

Figure 10:
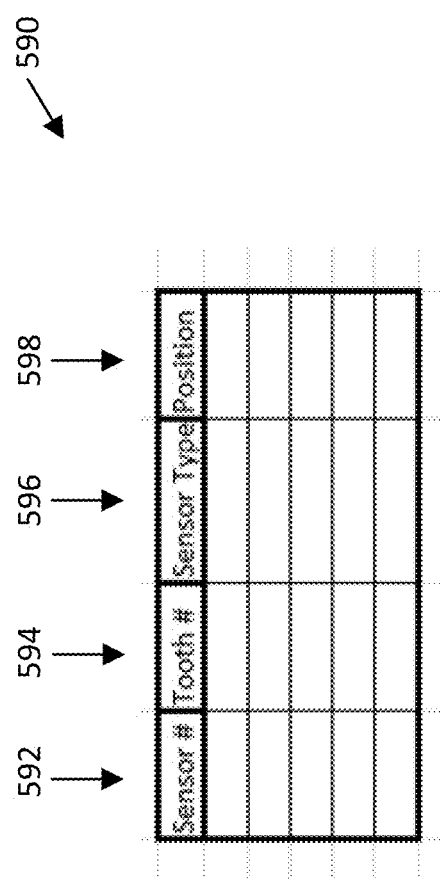
FIG. 10 is an example sensor data table that is stored in the memory of some embodiments of the dental appliance of FIG. 1.

FIG. 10 is an example sensor data table 590 that is stored in the memory 288 of some embodiments of the dental appliance 112. The sensor data table 590 stores information about the sensors 348a-f in the dental appliance 112. In some embodiments, the sensor data table 590 is stored in the computing device 116.

In the sensor data table 590, the first column 592 stores a sensor identification value, such as a sensor number. In some embodiments, the sensor identification value stored in the first column 592 correlates to a sensor identification value stored in the first column 562 of the measurement data table 560.

The second column 594 stores a tooth number corresponding to the tooth in the dentition of the patient P that a sensor is adjacent to when the dental appliance is worn by the patient P. In this manner, the measurements recorded by that sensor can be associated with a particular tooth. However, some embodiments do not include the second column 594.

The third column 596 stores a sensor type value representing the type of the sensor. In some embodiments, the sensor type value is used to interpret the measurement value stored in the second column 564 of the measurement data table 560. For example, in some embodiments, a conversion or compensation procedure may be performed on the measurement value stored in the second column 564 of the measurement data table 560 based on the sensor type value. However, some embodiments do not include the third column 596. For example, in some embodiments that include a single type of sensor the third column 596 is not included.

The fourth column 598 stores a position value representing the position of the sensor. In some embodiments, the position value is recorded as three-dimensional coordinate. In some embodiments, the position value is measured relative to the coordinate space of the digital model of the dentition of the patient P. In other embodiments, the position value is measured relative to a position of the dental appliance 112 (for example, the center of the dental appliance 112). In these embodiments, the position relative to the dental appliance 112 is then converted to a position relative to the dentition of the patient P during later processing (for example, by the data capture and analysis engine 118). In this manner, the measurements recorded by that sensor are associated with a particular position on the dentition of the patient P.

In operation, the sensor data table 590 is populated with a record representing each of the sensors in the dental appliance 112. Further, in some embodiments, the sensor data table 590 includes additional, fewer, or different columns.

Figure 11:
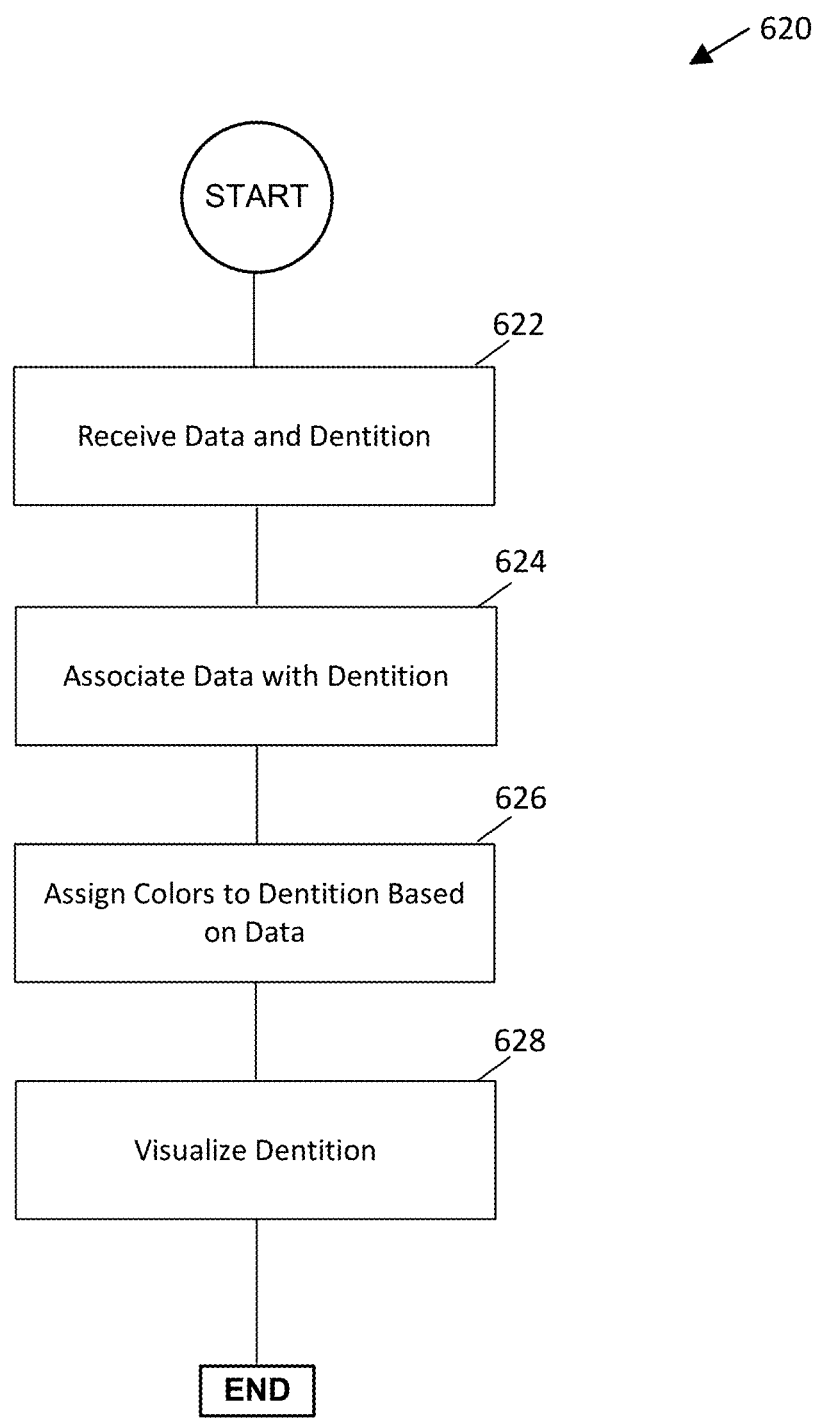
FIG. 11 is an example process of analyzing data from the dental appliance of FIG. 1.

FIG. 11 is an example process 620 of analyzing data from the dental appliance 112. In some embodiments, process 620 is performed by the data capture and analysis engine 118.

First, at operation 622, the sensor measurement data and dentition information is received. In some embodiments, the sensor measurement data includes the measurement data table 560 and the sensor data table 590, which are illustrated and described in more detail in FIG. 9 and FIG. 10 respectively. In some embodiments, the dentition is received as the digital model formed in operation 224 of the example process 220 of fabricating the dental appliance 112, which is illustrated and described in more detail with respect to FIG. 3.

Next, at operation 624, the sensor measurement data is associated with the dentition of the patient. In some embodiments, this operation is performed by mapping the position data of the sensor from the sensor data table 590 to the dentition. The measurements from the measurement data table 560 are then mapped to the position of the sensor on the dentition. In some embodiments, a data table that maps the sensor measurements to the dentition is generated during this operation. An example of this table is illustrated and described in greater detail with respect to FIG. 12.

Next at operation 626, colors are assigned to the dentition based on one or more of the properties in the sensor measurement data. For example, in some embodiments, the colors are assigned based on the maximum pressure measured by the sensor. In some embodiments, a first color is assigned when the maximum pressure measured is less than or equal to 150 MPa, a second color is assigned when the maximum pressure measured is greater than 150 MPa and less than or equal to 250 MPa, and a third color is assigned when the maximum pressure measured is greater than 250 MPa. In some embodiments, more or fewer colors are assigned. Additionally, in some embodiments, different threshold values are used. In some embodiments, the threshold values are selected based on the material strength of potential dental restoration materials. Further, in some embodiments, different methods of visually indicating the values measured are used, such as shading, circling, or texturing regions of the dentition. Still other embodiments are possible as well.

Additionally, in some embodiments, the colors (or other visual indicators) are assigned based on different properties, such as acceleration or tooth movement. In some embodiments that include multiple sensor types, multiple colors representing different properties are assigned to regions of the dentition.

Next, at operation 628, the dentition is visualized with the colors (or other visual indicators). In this manner, a user, such as the dentist D, can quickly evaluate and understand the pressures or other properties measured by the dental appliance 112. An example of the visualized dentition is illustrated and described with respect to FIG. 13.

Figure 12:
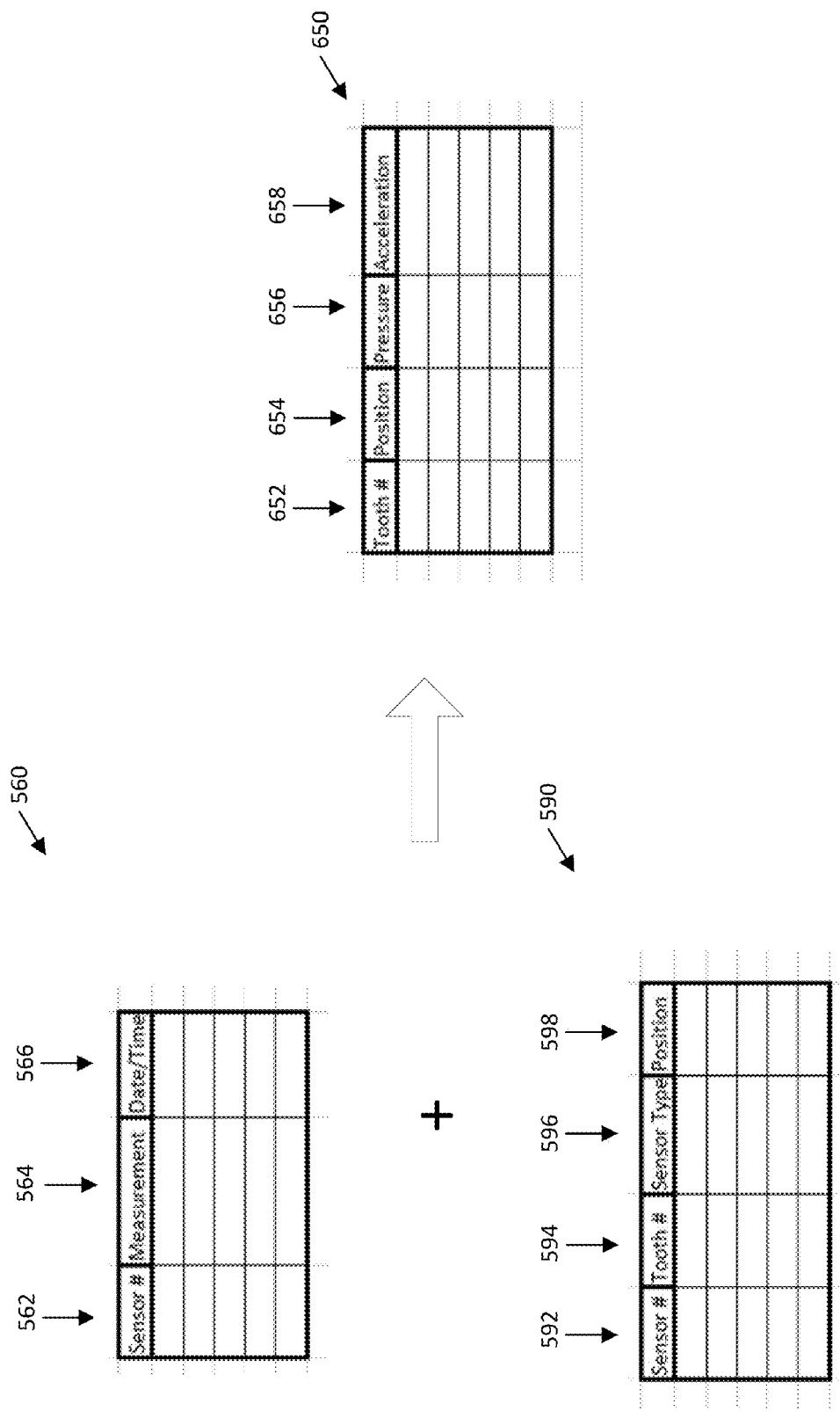
FIG. 12 illustrates an example dentition data table and an example process of computing the dentition data table by the data capture and analysis engine of FIG. 1.

FIG. 12 illustrates an example dentition data table 650 and an example process of computing the dentition data table 650 by the data capture and analysis engine 118.

In some embodiments, the records in the dentition data table 650 are calculated by operation 624 of the example process 620 of analyzing data from the dental appliance 112. For example, a record in the dentition data table 650 is generated by combining a record from the measurement data table 560 with an associated record in the sensor data table 590. For example, in some embodiments, a record in the measurement data table 560 is combined with a record in the sensor data table 590 when the sensor number values of the records match (e.g., the value in the first column 562 of the measurement data table 560 is the same as the value in the first column 592 of the sensor data table 590).

In the dentition data table 650, the first column 652 stores a tooth number corresponding to the tooth in the dentition of the patient P that the measurement corresponds to. In some embodiments, the value in the first column 652 is from the second column 594 of the sensor data table 590. However, some embodiments do not include the first column 652.

The second column 654 stores the position at which the measurement was recorded. In some embodiments, the position value is recorded as a three-dimensional coordinate that maps to a position on the surface of the dentition of the patient P. In some embodiments, the value in the second column 654 is from the fourth column 598 of the sensor data table 590. Further, in some embodiments, the value in the fourth column 598 of the sensor data table 590 is converted into the coordinate space of the dental model before being stored in the second column 654.

The third column 656 stores a pressure value corresponding to the pressure measured by the sensor. Similarly, the fourth column 658 stores an acceleration value corresponding to the acceleration measured by the sensor. In some embodiments, the values in the third column 656 and the fourth column 658 are from the second column 564 of the measurement data table 560. For example, depending on the sensor type value in the third column 596 of the sensor data table 590, the measurement value in the second column 564 of the measurement data table 560 is stored as either the pressure value in the third column 656 or the acceleration value in the fourth column 658. In some embodiments, the values stored in the third column 656 and the fourth column 658 are calculated by applying a conversion or compensation process to the measurement value recorded in the second column 564 of measurement data table 560. In this manner, the measurement value stored in the second column 564 of the measurement data table 560, which in some embodiments is a raw sensor value, is converted to a measurement in units that are meaningful to a typical observer.

In some embodiments, the dentition data table 650 is stored in the computing device 116. Further, in some embodiments, the dentition data table 650 includes additional, fewer, or different columns.

Figure 13:
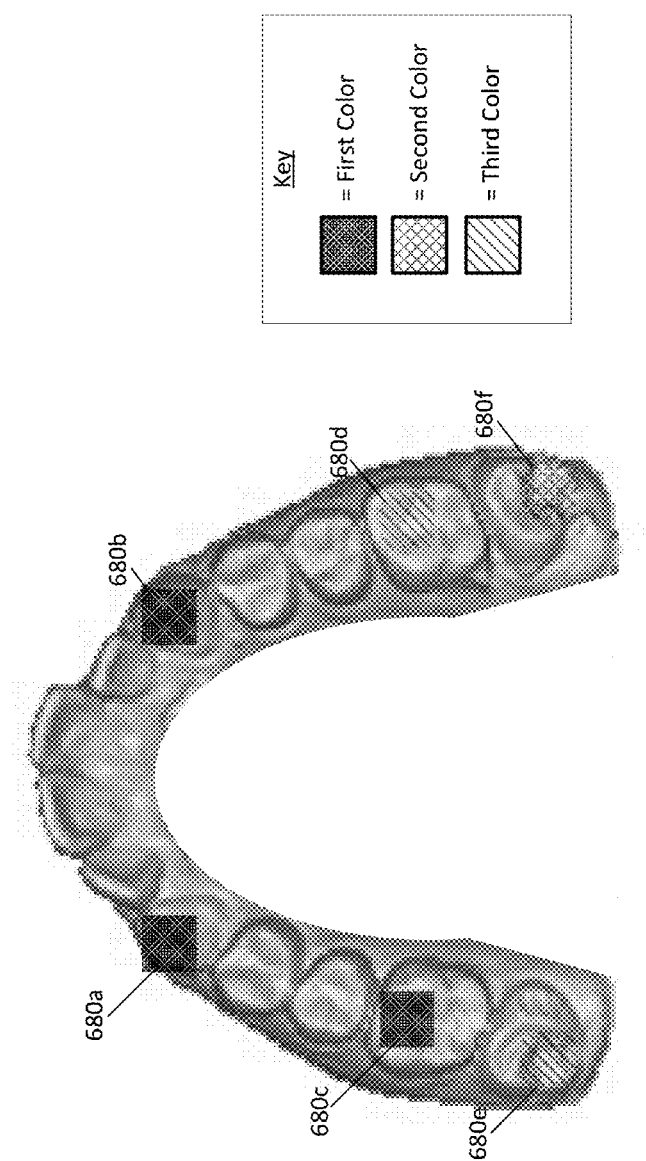
FIG. 13 illustrates an example dental property map of FIG. 1.

FIG. 13 illustrates an example dental property map 120. The dental property map 120 includes regions 680a-f corresponding to the locations of the sensors 348a-f in the dental appliance 112. Each of the regions 680a-f are highlighted with a color (or other visual indicator) that is associated with a different value or range of values for the property being visualized. For example, regions 680a-c are colored a first color, regions 680d-e are colored a second color, and region 680f is colored a third color. In some embodiments, these colors correspond to the pressure measured in the region.

Figure 14:
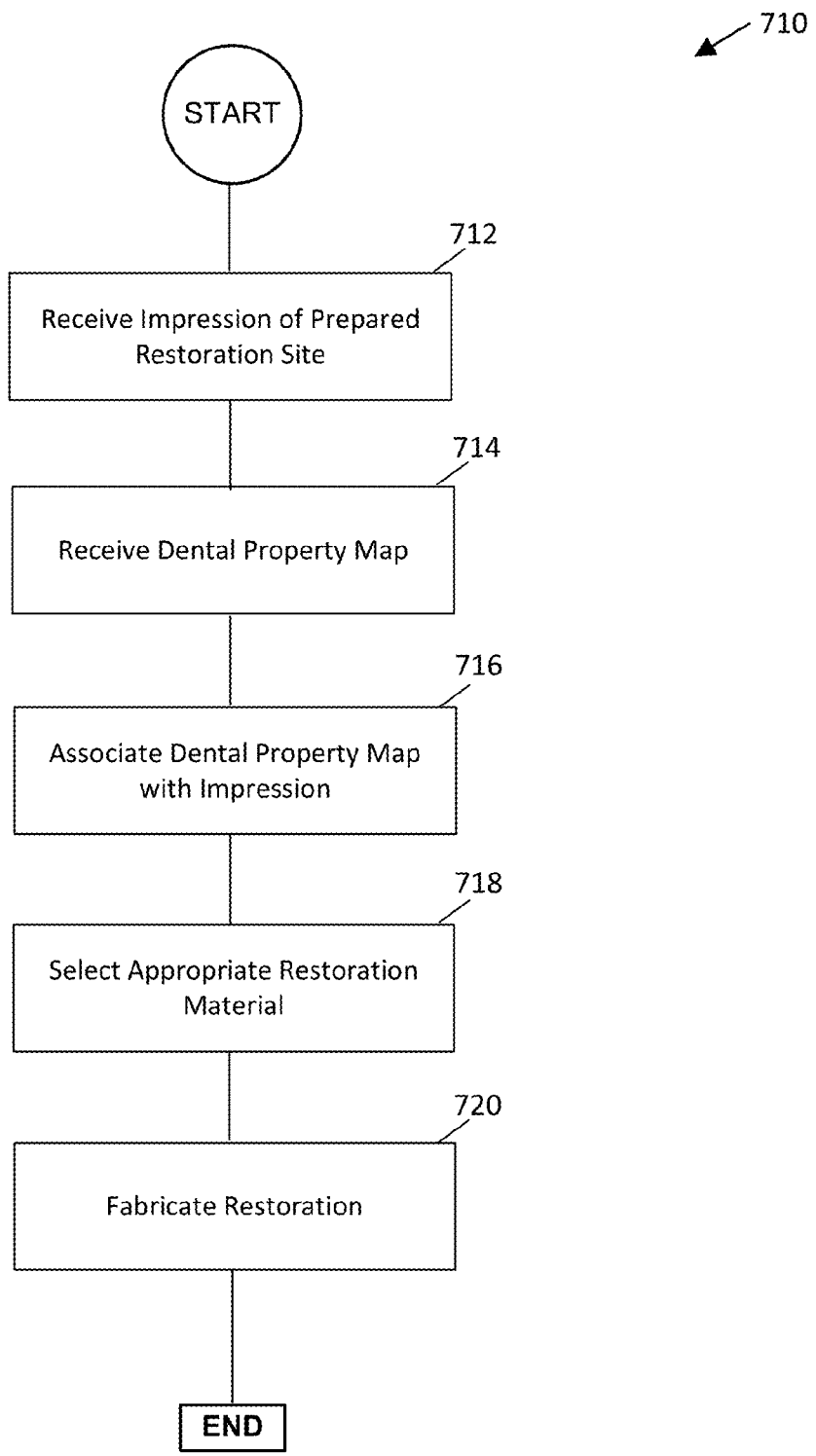
FIG. 14 is an example process of fabricating a dental restoration using data from the dental appliance of FIG. 1.

FIG. 14 is an example process 710 of fabricating a dental restoration 124 using data from the dental appliance 112. In some embodiments, the process 710 is performed by the restoration fabrication station 122.

Initially, at operation 712, an impression of the prepared restoration site is received. Examples of a prepared restoration site include a tooth or series of teeth that the dentist D has prepared (i.e., removed tooth material) to receive a restoration such as a filling, partial crown, full crown, veneer, or bridge. In some embodiments, the dental property map 120 is generated before the dentist D prepares the restoration site. Accordingly, in those embodiments, the impression received at operation 712 is different than the dental impression 106.

Next, at operation 714, the dental property map 120 is received. In some embodiments, the dental property map 120 is received as an image. In other embodiments, the dental property map 120 is received as three-dimensional model data, including the associated measured property values.

Next, at operation 716, the dental property map 120 is associated with the impression of the prepared restoration site. In some embodiments, this is performed by simply visually inspecting the dental property map 120 to determine the value of the property at the location for the dental restoration 124. In other embodiments, the dental property map 120 is imported into a computer aided design (CAD) program and aligned with the coordinate system of the impression of the prepared restoration sites.

Next, at operation 718, an appropriate restoration material is selected based on the impression of the prepared restoration site and the dental property map 120. In some embodiments, the restoration material is selected based on the maximum pressure recorded at the location of the restoration. In other embodiments, the restoration material is selected based on a combination of the pressure recorded at the location of the restoration and the space available for the restoration between the prepared restoration site and the opposing dentition. This is beneficial for restoration materials that have varying strength properties based on thickness.

Further, in some embodiments, the geometry of the prepared restoration site, the design of the dental restoration 124, pressure data from the dental property map 120, and the properties of a potential restoration material are analyzed using finite element analysis to determine whether the dental restoration is likely to withstand the pressures it will be subjected to after being seated in the dentition of the patient P.

Next, at operation 720 the dental restoration 124 is fabricated. In some embodiments, the dental restoration 124 is fabricated using a CAD program, along with a rapid fabrication machine. In other embodiments, the dental restoration 124 is fabricated using the lost-wax technique, porcelain build-up technique, ceramic press technique, or any other dental restoration fabrication technique.

Figure 15:
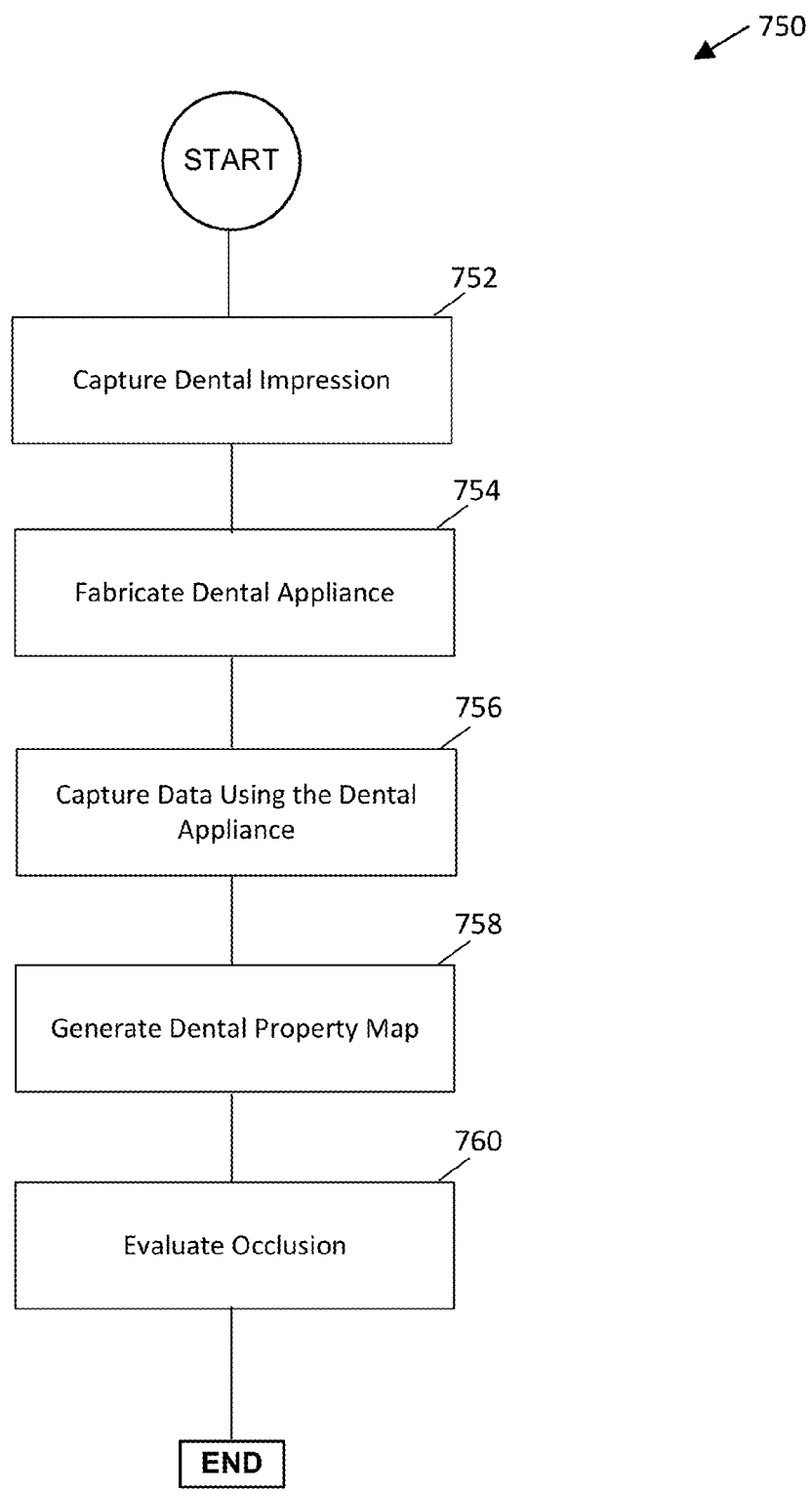
FIG. 15 is an example process of operating the system of FIG. 1 to evaluate the occlusion of a patient.

FIG. 15 is an example process 750 of operating the system 100 to evaluate the occlusion of a patient.

At operation 752, the dental impression 106 of the patient is captured. At operation 754, the dental appliance 112 is fabricated. At operation 756, data is captured using the dental appliance 112. At operation 758, the dental property map 120 is generated.

At operation 760, the occlusion of the patient is evaluated using the dental property map 120. In some embodiments, operation 760 is performed by the dentist D at the dental office 102 using a computing device. For example, in some embodiments, the dentist D uses a computing device associated with the dental impression station 104 to evaluate the occlusion of the patient.

In some embodiments, the dentist D evaluates the occlusion of the patient P by reviewing the dental property map 120 to identify regions of the dentition of the patient that are subject to larger forces. Using this information, the dentist D may determine whether additional treatment is necessary for the patient P. Additionally, the dentist D may determine to monitor a particular region of the dentition at future visits. In some of these embodiments, the system 100 is used as a diagnostic tool regardless of whether the patient is having restorative work performed.

Figure 16:
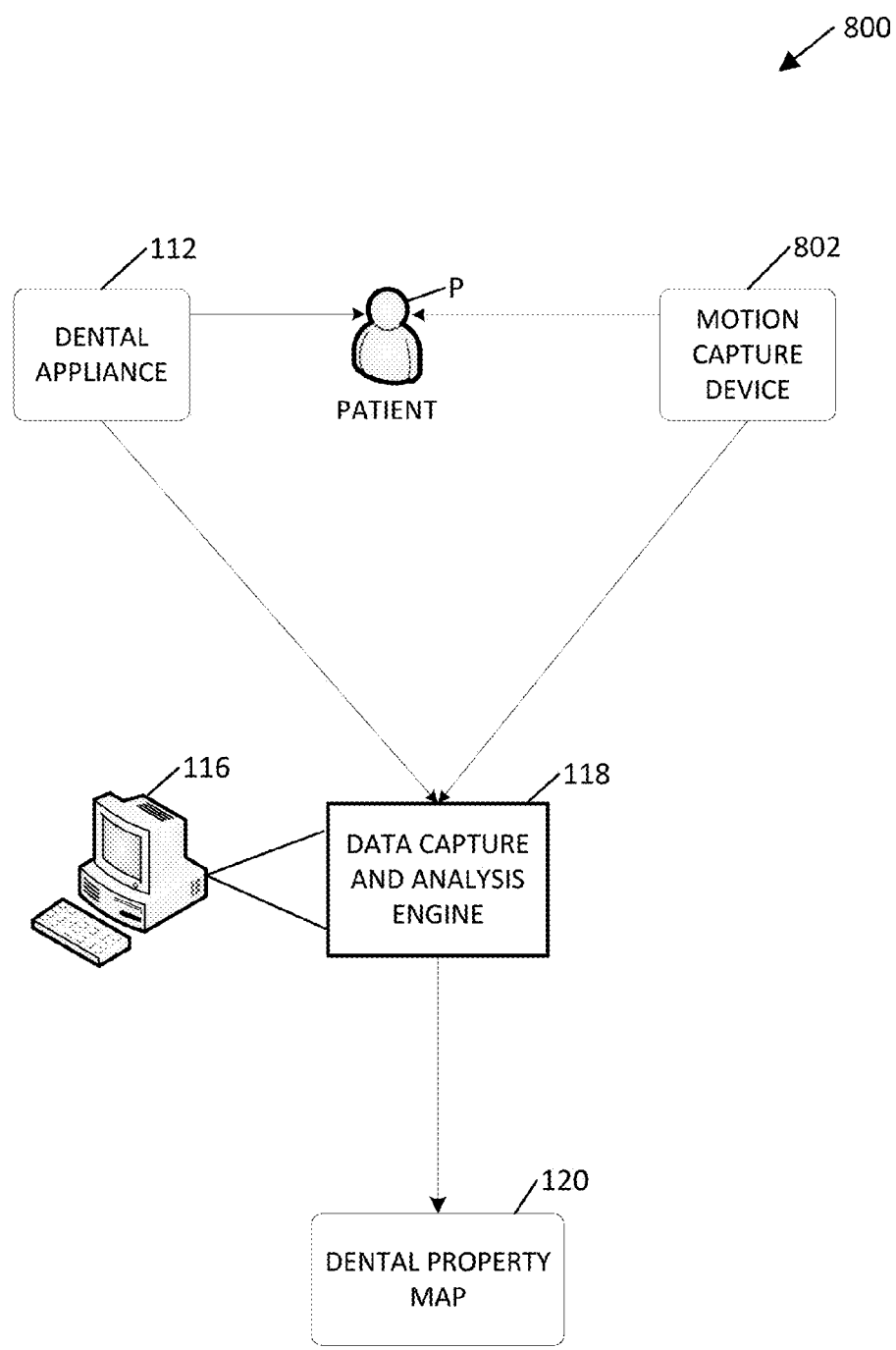
FIG. 16 is a schematic block diagram illustrating an example of a system for evaluating the dentition of a patient using the dental appliance for measuring teeth movement and interference of FIG. 1.

FIG. 16 is a schematic block diagram illustrating an example of a system 800 for evaluating the dentition of a patient P using a dental appliance 112 for measuring teeth movement and interference. In this example, the system 800 includes a dental appliance 112, motion capture device 802, computing device 116 including a data capture and analysis engine 118, and dental property map 120.

The system 800 is similar to the system 100, except that it includes the motion capture device 802. The system 800 can be used in the same ways and for the same purposes as the system 100. However, in some embodiments, the system 800 can additionally be used to evaluate the dentition opposite the dental appliance 112. For example, in some embodiments, the dental appliance 112 is worn on the maxillary arch and the dental property map is generated for the mandibular arch. Alternatively, in some embodiments, the dental appliance 112 is worn on the mandibular arch and the dental property map is generated for the maxillary arch.

The motion capture device 802 captures data associated with the movement of the dental arches relative to each other. In some embodiments, the motion capture device 802 operates using optical information to determine the relative movement of the dental arches. Additionally, in some embodiments, the motion capture device 802 also captures the positions relative to each other.

In some embodiments, the motion capture device 802 captures the data relating to the relative movement of the dental arches during some or all of the time the dental appliance 112 captures pressure data.

In some embodiments, the data capture and analysis engine 118 receives data from both the dental appliance 112 and the motion capture device 802. In some embodiments, the data capture and analysis engine 118 combines the data from the dental appliance 112 with the data from the motion capture device 802 to determine the pressure experienced on the arch opposite the dental appliance 112. For example, in some embodiments, uses the data from the motion capture device 802 to determine the position is on the opposing dentition that is in contact with a sensor in the dental appliance 112 at a particular time. Using this information, the data capture and analysis engine 118 is then able to determine the pressure on that surface at that particular time.

In some embodiments, the data capture and analysis engine 118 temporally offsets the data received from the motion capture device 802 by a negative or positive amount to ensure that it is properly aligned with the data captured by the dental appliance 112. In some embodiments, the correct temporal offset is determined using a calibration procedure.

The system 800 may be particularly beneficial for evaluating the occlusion of the arch opposite the dental appliance 112 repeatedly as treatment is being performed on that arch. In some embodiments, it is not necessary to refabricate the dental appliance 112 when the opposing arch is modified during treatment. For example, in some embodiments, the dental appliance 112 is fabricated before any treatment has been performed and is configured to be worn on the maxillary arch. The system 800 is then used as a diagnostic tool to evaluate the occlusion of the mandibular arch. The information captured by the system 800 may also be used to fabricate a restoration. Later, after the dentition of the mandibular arch has been modified (e.g., by installing a dental restoration), the dental appliance 112 can still be worn on the maxillary arch because the maxillary arch has not been modified. The system 800 can then be used to evaluate the occlusion of the mandibular arch after the restoration has been installed.

Additionally, in some embodiments of the system 800, the data capture and analysis engine 118 generates a dental property map 120 that illustrates how the occlusion of the patient has changed by installing the restoration.

Figure 17:
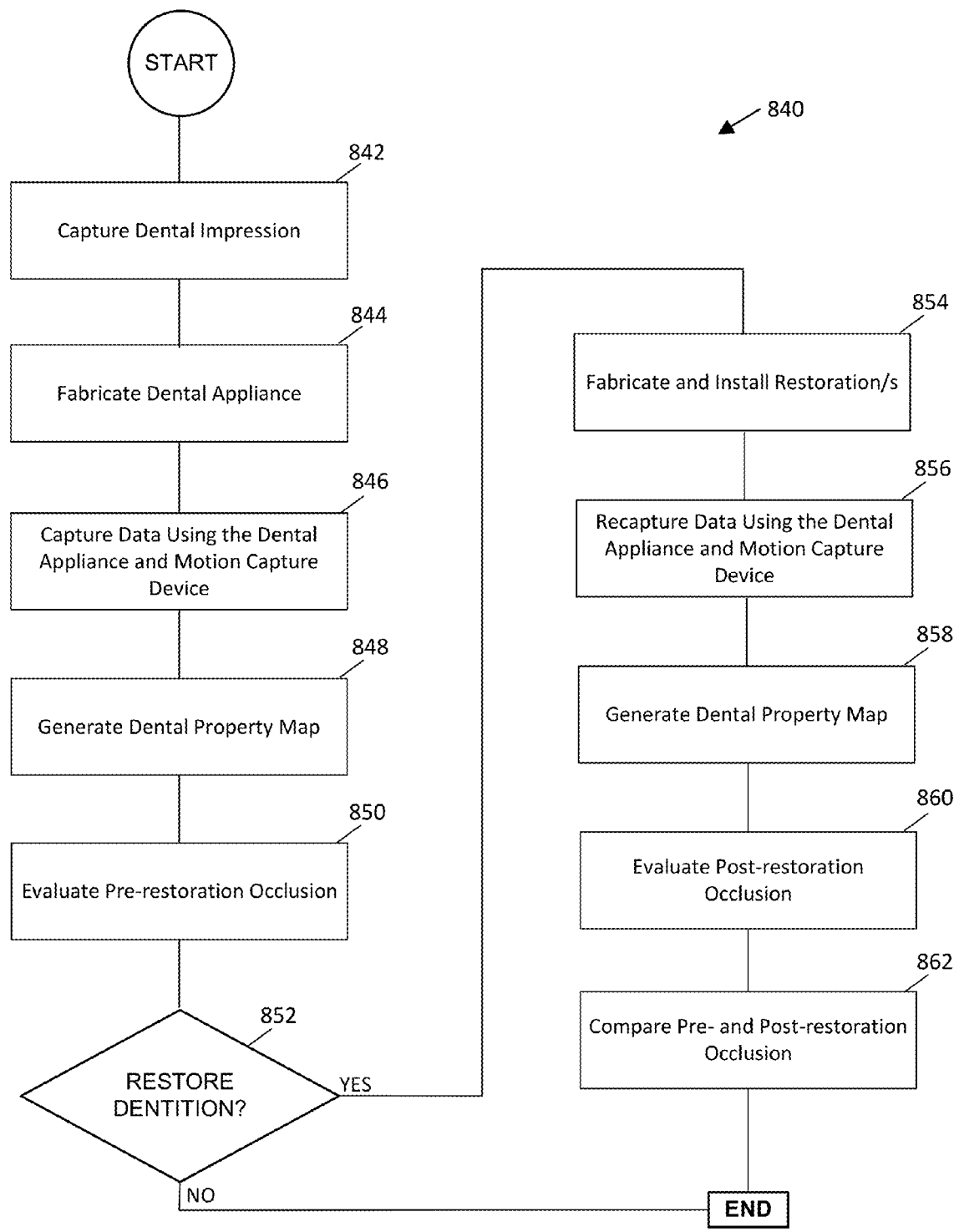
FIG. 17 is an example process of operating the system of FIG. 16 to evaluate the restored dentition of a patient.

FIG. 17 is an example process 840 of operating the system 800 to evaluate the restored dentition of a patient.

Initially, at operation 842, a dental impression 106 is captured. At operation 844, the dental appliance 112 is fabricated. At operation 846, data is captured using the dental appliance 112 and the motion capture device 802. At operation 848, the dental property map 120 is generated.

At operation 850, the pre-restoration occlusion is evaluated. In some embodiments, the pre-restoration occlusion is evaluated using the dental property map 120.

At operation 852, the dentist D determines whether the dentition of the patient P needs to be restored. In some embodiments, the dentist D determines that the patient P needs restorative work based, in part, on the dental property map 120. In other embodiments, the dentist D determines that the patient P needs restorative work based on other factors. If the dentist D determines that the patient P needs one or more restorations, the process 840 continues to operation 854. If not, the process 840 ends.

At operation 854, one or more dental restoration 124 is fabricated and installed. At operation 856, data is recaptured using the dental appliance 112 and the motion capture device 802. In some embodiments, the same dental appliance 112 is used to capture data both pre- and post-restoration. This is possible because the system 800 uses motion data to create a dental property map 120 for the arch opposite of the dental appliance 112. Accordingly, in some embodiments, when the opposite arch is restored, the dental appliance 112 will still fit and record data.

At operation 858, a dental property map based on the post-restoration data is generated. At operation the 860, the post-restoration occlusion is evaluated. In some embodiments, the dentist D will evaluate the post-restoration occlusion to predict patient comfort and future dental wear patterns.

At operation 862, the pre- and post-restoration occlusions are compared. In some embodiments, the data capture and analysis engine 118 generates a color map based on the changes to the occlusion of the patient. For example, if the pressure recorded at a particular point decreased post-restoration, that particular point would be shaded a first color. Additionally, if the pressure recorded at another particular point increased post-restoration, that particular point would be shaded a second color. In this manner, the dentist D is able to evaluate how the restoration changed the occlusion of the patient P.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A wearable dental appliance for capturing dental properties of a patient comprising:
    a support structure configured to be worn by the patient on a dentition of the patient; and
    at least one pressure sensor coupled to the support structure, wherein the at least one pressure sensor is configured to capture a series of numerical measurements of pressure at a location on an occlusal surface of the dentition of the patient, the measurements being associated with one or more tooth numbers and one or more three-dimensional positions on the surface of teeth of the patient's dentition.

2. The wearable dental appliance of claim 1, further comprising a processing device and a computer-readable storage device, wherein the processing device is configured to receive the measurements and to store the measurements on the computer-readable storage device.

3. The wearable dental appliance of claim 2, wherein the computer-readable storage device comprises flash memory.

4. The wearable dental appliance of claim 2, wherein the computer-readable storage device stores a sensor location table that associates the at least one sensor with a location on the dentition of the patient and wherein the sensor-location table is used to associate the measurements with one or more locations on the dentition of the patient.

5. The wearable dental appliance of claim 1, wherein the dental property is contact pressure.

6. The wearable dental appliance of claim 1, wherein the dental property is acceleration.

7. The wearable dental appliance of claim 1, wherein the dental property is movement.

8. The wearable dental appliance of claim 1, wherein the at least one sensor comprises an accelerometer.

9. The wearable dental appliance of claim 8, wherein the piezoelectric pressure sensor is formed from a film of piezoelectric material.

10. The wearable dental appliance of claim 1, wherein the at least one sensor comprises a piezoelectric pressure sensor.

11. A system for capturing dental properties of a patient comprising:
    a wearable dental appliance comprising:
        a support structure configured to be worn by the patient on a dentition of the patient; and
        at least one pressure sensor coupled to the support structure, wherein the at least one pressure sensor is configured to capture a numerical measurement of pressure at a location on an occlusal surface of the dentition of the patient; and
    a computing device comprising a processing device, computer readable storage device, the computer readable storage device storing data instructions which, when executed by the processing device, cause the processing device to:
        receive measurements from the wearable dental appliance;
        associate the measurements with tooth numbers and three-dimensional positions on the surface of teeth of the patient's dentition;
        generate a dental map, wherein the dental map is configured to display at least some of the measurements on an image of at least a portion of the dentition of the patient.

12. The system of claim 11, wherein the computing device receives the measurements from the wearable dental appliance wirelessly.

13. The system of claim 12, further comprising a motion capture device, wherein the motion capture device is configured to capture motion data associated with the movement of mandibular dental arch of the dentition of the patient relative to the maxillary dental arch of the patient.

14. The system of claim 13, wherein the computing device associates the measurements with locations on the dentition of the patient using the motion data.

15. The system of claim 11, wherein the dental map show at least some of the measurements on an image of at least a portion of the dentition of the patient by displaying a color associated with a value measured at a location on the at least a portion of the dentition associated with the measurement.

16. The system of claim 11, wherein the computing device displays the dental map.

17. The system of claim 11, further comprising a second computing device, wherein the second computing device is configured to receive and display the dental map.

18. A method of restoring the dentition of a patient comprising:
    capturing an impression of the dentition of the patient;
    fabricating a dental appliance to be worn on at least a portion of the dentition of the patient, wherein the dental appliance includes at least one pressure sensor configured to capture numerical measurements of pressure at a location on an occlusal surface of the dentition of the patient;
    using the dental appliance to capture measurement data while the patient is wearing the dental appliance, wherein the measurement data comprises a plurality of measurements captured by the one or more sensors;
    associating the measurement data with one or more tooth numbers and one or more three-dimensional positions on the surface of teeth of the patient's dentition;

selecting a restoration material based in part on the measurement data; and fabricating a dental restoration for the patient, wherein the dental restoration is formed, at least in part, from the selected restoration material.

19. The method of claim 18, wherein the dental appliance is worn on a first dental arch of the dentition of the patient, and the measurements are associated with locations on a second dental arch of the dentition of the patient.

20. The method of claim 18, wherein the dental appliance is worn on a first dental arch of the dentition of the patient, and the measurements are associated with locations on the first dental arch of the dentition of the patient.

* * * * *